(12) United States Patent
Martz et al.

(10) Patent No.: US 12,194,176 B2
(45) Date of Patent: *Jan. 14, 2025

(54) SYSTEM AND DEVICE FOR SANITIZING PERSONAL USE ITEMS

(71) Applicant: Clean Light Laboratories LLC, Scottsdale, AZ (US)

(72) Inventors: Carrie Martz, Scottsdale, AZ (US); Brooke O'Connor, Scottsdale, AZ (US)

(73) Assignee: Clean Light Laboratories LLC, Scottsdale, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/531,413

(22) Filed: Dec. 6, 2023

(65) Prior Publication Data

US 2024/0100207 A1    Mar. 28, 2024

Related U.S. Application Data

(63) Continuation of application No. 16/526,754, filed on Jul. 30, 2019, now Pat. No. 11,839,691, which is a
(Continued)

(51) Int. Cl.
| | |
|---|---|
| *A61L 2/10* | (2006.01) |
| *A61L 2/08* | (2006.01) |
| *A61L 2/14* | (2006.01) |
| *A61L 2/24* | (2006.01) |
| *G06F 3/14* | (2006.01) |
| *H02J 7/00* | (2006.01) |
| *G01G 19/52* | (2006.01) |
| *G06F 3/04847* | (2022.01) |

(52) U.S. Cl.
CPC ............... *A61L 2/10* (2013.01); *A61L 2/085* (2013.01); *A61L 2/24* (2013.01); *A61L 2/14* (2013.01); *A61L 2202/122* (2013.01); *A61L 2202/14* (2013.01); *A61L 2202/182* (2013.01); *G01G 19/52* (2013.01); *G06F 3/04847* (2013.01); *G06F 3/14* (2013.01); *H02J 7/0042* (2013.01)

(58) Field of Classification Search
CPC ... A61L 2/10; A61L 2/085; A61L 2/24; A61L 2202/14; A61L 2202/182
USPC .......................... 250/453.11, 454.11, 455.11
See application file for complete search history.

(56) References Cited

U.S. PATENT DOCUMENTS

| | | |
|---|---|---|
| 3,478,758 A | 11/1969 | Davies |
| 7,520,978 B2 | 4/2009 | Harbers |

(Continued)

*Primary Examiner* — Nicole M Ippolito
(74) *Attorney, Agent, or Firm* — Zeman-Mullen & Ford, LLP

(57) ABSTRACT

A system and apparatus for sanitizing person use items. The system is comprised essentially of a mechanism for emitting sanitizing electromagnetic radiation within an enclosed compartment. The apparatus may be light-tight such that the radiation is contained within the apparatus. It may be configured to emit a plurality of sanitizing wavelengths. The apparatus may include a series of reflective and/or refractive apparatuses to alter the reflection path of the emitted electromagnetic radiation, allowing the electromagnetic radiation to reflect in a plurality of directions. The enclosure may include a support member or personal item support that may be transparent to, or reflective of, the electromagnetic radiation.

20 Claims, 23 Drawing Sheets

Related U.S. Application Data continuation of application No. 16/119,344, filed on Aug. 31, 2018, now Pat. No. 10,549,001, which is a continuation-in-part of application No. 15/206,088, filed on Jul. 8, 2016, now abandoned.

(60) Provisional application No. 62/190,064, filed on Jul. 8, 2015.

(56) References Cited

U.S. PATENT DOCUMENTS

| | | |
|---|---|---|
| 7,560,706 B1 | 7/2009 | Castelluccio |
| 7,921,578 B2 | 4/2011 | McAllister et al. |
| 8,481,970 B2 | 7/2013 | Cooper et al. |
| 8,964,405 B2 | 2/2015 | La Porte et al. |
| 9,339,105 B2 | 5/2016 | Levy et al. |
| 9,550,004 B2 | 1/2017 | Smetona et al. |
| 9,717,809 B2 * | 8/2017 | Martz .................. H02J 7/0042 |
| 10,058,169 B2 | 8/2018 | Gorelick |
| 10,549,001 B2 * | 2/2020 | Martz .................... A61L 2/085 |
| 11,839,691 B2 * | 12/2023 | Martz .................... A61L 2/085 |
| 2007/0075268 A1 | 4/2007 | Harris |
| 2009/0225286 A1 | 9/2009 | Nagasaka et al. |
| 2011/0001060 A1 | 1/2011 | Welker |
| 2013/0256560 A1 | 10/2013 | Yerby |
| 2016/0302567 A1 | 10/2016 | Gorelick |
| 2016/0354503 A1 | 12/2016 | Hutchens et al. |

\* cited by examiner

SYSTEM AND DEVICE FOR SANITIZING PERSONAL USE ITEMS

CROSS-REFERENCE TO RELATED APPLICATIONS

This application is a continuation application and claims the benefit of, and priority to, U.S. patent application having Ser. No. 16/526,754, filed on Jul. 30, 2019, which is a continuation of U.S. patent application having Ser. No. 16/119,344, now issued U.S. Pat. No. 10,549,001, which is a continuation-in-part patent application of patent application having Ser. No. 15/206,088, filed Jul. 8, 2016, which claims the benefit of, and priority to U.S. provisional patent application having Ser. No. 62/190,064, filed Jul. 8, 2015, which are hereby incorporated by reference in their entireties.

FIELD OF THE INVENTION

This application relates generally to storing and sanitizing devices, and, more specifically, to storing, sanitizing, and charging devices with complex shapes. More particularly, this application relates to an apparatus for sanitizing personal use items which includes at least one enclosure having an upper member and a lower member, at least one emitter configured to emit electromagnetic radiation disposed within at least one of the upper member or lower member, at least one reflective grid disposed in at least one of the upper member or the lower member where the reflective grid is configured to reflect the electromagnetic radiation in a plurality of directions, at least one power module configured to power the emitter(s), and at least one control module configured to control the apparatus.

BACKGROUND OF THE INVENTION

Devices such as children's toys, adult toys, cellular telephones, or even personal hygiene devices such as hairbrushes can be difficult to clean to a sanitary condition. Electronic elements of toys and mobile phones cannot be safely exposed to water, including alcohol based solutions. Some materials, such as silicones in adult toys, cannot be exposed to particular cleaning chemicals. Attempts have been made to overcome these problems, such as in U.S. Pat. No. 8,964,405. However, no solution to date has managed to overcome persistent problems, such as protection of the device and cleaning of complex shapes. For example, the system in the above referenced patent is designed only to receive and clean a mobile telephone or tablet like device, which would fail to sanitize the nooks and crannies found in children's toys, such as Lego® toys, or adult toys. These are just some of the problems which the present invention aims to overcome.

Technical materials which can be regarded as useful for the understanding, searching, and examination of the invention includes:
U.S. Pat. No. 5,964,405 (La Porte), "Portable electronic device sanitizer", 2015; and
U.S. Pat. No. 8,203,124 (Havens), "Sterilization apparatus", 2012.

The foregoing disclosures are hereby incorporated by reference as if fully set forth herein.

SUMMARY OF THE INVENTION

This application relates generally to storing and sanitizing devices, and, more specifically, to storing, sanitizing, and charging devices with complex shapes.

The device sanitizer disclosed herein may be configured to expose a device for different amounts of time. Some types of electromagnetic radiation may be capable of sanitizing the surface of a device relatively quickly (for example, 3-5 minutes of exposure to UV-C may be sufficient to sanitize some surfaces). In some embodiments, the electromagnetic radiation exposure time may be adapted in accordance with the intensity of the emitted electromagnetic radiation, type (s) of electromagnetic radiation used to irradiate the device, user configuration and/or preferences, or the like. In some embodiments, the type and amount of electromagnetic exposure is configurable by a user (e.g., via button, timer, display device, user-selectable manufacturer presets, or other user interface component). In some embodiments, the amount of exposure may be automatically determined based upon properties of the electromagnetic radiation, time since a last sanitization cycle for the device, and/or other suitable factors. Alternatively, or in addition, the type and amount of exposure may be calculated by a user entry pertaining to at least one of a material, structure, or brand associated with the device to be sanitized.

In some embodiments, the electromagnetic radiation used may be configured to target a specific organism (such as a specific type of bacteria). The particular wavelength may also be selected to avoid damage to the device (e.g., may be selected to avoid damaging the finish, materials, case, and/or operational components of the OED). For example, the electromagnetic radiation wavelengths may be selected to sterilize hard plastics, while minimizing harm to the silicones, composites, metals, alloys, fabrics, pigments or dyes used in the construction of the device. In some embodiments, wavelengths may be selected to minimize penetration of the electromagnetic radiation into the interior of the device and/or wavelengths that will not adversely affect electronics, processor, memory, storage, and/or other components of the device. Conversely, in some embodiments, wavelengths may be selected specifically for their penetrative values, allowing for a more thorough sanitization of, for example, porous materials or materials that may harbor moisture and with it certain bacteria or molds.

The device sanitizer disclosed herein may be configured to sanitize any number of different types of devices, including, but not limited to: a portable telephone, a cordless telephone, a smart phone, a wireless headset, a portable media device, a digital camera, a video recorder, an audio recorder, a portable gaming device, a portable computing device, a tablet computer, laptop computer, notebook computer, an electronic reading device, a personal digital assistant (PDA), a palmtop computer, a handheld computer, a pen computer, a ultra-mobile personal computer, a pager, a portable navigation device, a personal navigation assistant (e.g., portable Global Positioning System (GPS) unit), or the like. The device sanitizer may also sanitize personal use items such as baby bottles, water bottles, cosmetics, pacifier's, thermometers, dental apparatus and tools, artificial teeth, cosmetic brushes and cosmetic application tools, combs, dermatology aids, eye wear and eye tools, professional beauty and aesthetician tools, sport gloves and devices, earphones and earpieces, and other medical and household personal use items.

The device may also be configured to hold multiple devices, including configurations to keep multiple devices separate. More importantly, the device may also be configured to sanitize complex shapes, such as those of children's or adult toys, allowing for the electromagnetic radiation to penetrate into curves, angles, holes, ports, etc., of complex shapes. Such embodiments may include reflective aspects, refractive aspects, and elements configured to hold the devices to be sanitized in particular places or orientations.

As disclosed herein, an apparatus for sanitizing a device may comprise an interior enclosure or compartment configured to receive a device and a sanitizing module comprising one or more electromagnetic emitters. The apparatus may further comprise a support member configured to maintain the device at a particular orientation and/or position within the enclosure. In some embodiments, the support member may be transparent (or substantially transparent) to the electromagnetic radiation emitted by the electromagnetic emitters and/or the interior surface of the enclosure may be configured to reflect electromagnetic radiation, such that the electromagnetic emitter is capable of irradiating the entire surface of the device. The apparatus may further comprise a charging module configured to charge the device while the device is within the enclosure or compartment (and/or while the device is being sanitized by the electromagnetic radiation). In some embodiments, the apparatus may comprise one or more indicators configured to display sanitization and/or charging status information to a user.

The apparatus may be configured to limit activation of the sanitization module (and/or electromagnetic emitters). In some embodiments, the electromagnetic emitters may be configured to emit electromagnetic radiation in response to determining that the enclosure is in a closed configuration. As used herein, a "closed" or "sealed" configuration refers to a configuration in which the interior region, portion, and/or compartment of the apparatus is closed with respect to the transmission of electromagnetic radiation, such that there is no transmission path from the interior of the apparatus to the exterior of the apparatus and/or electromagnetic radiation of the emitter is not radiated to the exterior of the apparatus (e.g., the electromagnetic radiation does not escape the interior compartment). By contrast, in an "open" configuration, the interior of the apparatus is accessible, such that electromagnetic radiation emitted therein would be capable of radiating from the apparatus. In the open configuration, the device may be placed within the apparatus and/or removed from the apparatus.

In some embodiments, the device sanitization apparatus may comprise an open sensor configured to determine whether the apparatus is open or closed. The device sanitization apparatus may be configured to activate the sanitization module (e.g. electromagnetic emitter) in response to determining that the apparatus is in a closed or sealed configuration. The sanitization module may be deactivated in response to the open sensor determining that the apparatus is in an open or unsealed configuration. The open sensor may comprise one or more detection mechanisms including, but not limited to: contact switches, conductive switches, magnetic switches, capacitive switches, resistive switches, latches, or the like. In some embodiments, the open sensor may comprise a plurality of redundant detection mechanisms, and the sanitization module may be activated in response to each of the detection mechanisms indicating that the apparatus is in a closed or sealed configuration.

The apparatus may be further configured to limit activation of the sanitization module via detection in a change of weight. For example, if the apparatus has run a sanitization cycle, a weight sensor may register that the weight has not changed since the cycle run and the control module may prevent a second cycle until the weight sensor registers a change. This is useful for preventing the unauthorized use by children, who may find the apparatus and think it a toy. It is also useful to prevent the unwanted and unnecessary activation while the apparatus is in transit, such as in a suitcase, ultimately saving the power store for the apparatus from unnecessary drain.

In some embodiments, the device sanitization apparatus may comprise an enclosure comprising an upper portion and a lower portion. The upper and lower portions may form a clamshell, and may define an interior portion configured to receive the device. In some embodiments, an apparatus for sanitizing a device comprises an enclosure and a lid wherein the lid may be opened so that a device can be placed into the enclosure. In yet another embodiment the apparatus comprises an enclosure and a drawer wherein the drawer is configured to slide or rotate out of the enclosure so that a device can be placed therein. The drawer may comprise a tray or other support member configured to receive a device. In some embodiments, the tray comprises a rim, lip, or raised portion extending from the tray to prevent the device from sliding off the tray when the drawer is opened and/or closed.

Sanitation using the device may occur by using at least one of the following exemplary modes:
  A. Germicidal UV-C near the DNA absorption 260 nm;
  B. Thymine dimer UV-B near thymine absorption 280 nm with ozone;
  C. Combination of A and B;
  D. Intermittently switching between A and B with LED;
  E. Scanning narrowband 240-300 nm with QCL LED; and
  F. Scanning broadband 100-315 nm with QCL LED.

Switching between A and B modes may be more effective near the first few multiples and fractions of the Schumann resonance frequency (about 7.83 Hz), that is near 2, 4, 8, 16 and 31 Hz (+/−25%). Note that these modes are merely exemplary and that other modes and ranges may be used.

To assist in ozone production via UV light in the 280-315 nm band, the user may place a humidifying sponge and/or a humidifying wick within the enclosure along with the personal use item to be sanitized. Humidification may be assisted by ultrasound generated inside the enclosure. The ozone generation may also be assisted by providing at least one thin layer of ceramic ozone plate within the enclosure. These auxiliary devices may be smaller than the personal use item being sterilized and fit within, or are affixed within, the enclosure.

To assist in light scattering, a mirrored or reflective prismatic array liner, tray, or other support member may also be inserted into the enclosure which functions as a support for the item to be sanitized. In one exemplary embodiment, the device includes am item support member having a plurality of members extending from the item support. The plurality of members may be a plurality of raised parallel members that extend along the longest length of the item support member. The raised parallel members may be reflective and the item support member may be removable from the enclosure. In another exemplary embodiment, the plurality of members extending form the item support member may be transparent fibers and the item support member may include a base member having first and second ends extending upward from the base member with the plurality of transparent fibers extending form the first or second end of the base member. The first end of the base member may include a notch with the plurality of transparent fibers extending from the second end of the base member. The transparent fibers may take the form of a round brush with varying lengths of the transparent fibers forming the bristles of the round brush. Fiber optics may guide UV light from the emitter into the deepest part of brushes or similar items being sanitized. The item support member that functions as a brush holder may be used inside the enclosure of the device or outside the enclosure and may include an extension/retraction system and/or movement system for deep sanitization.

In yet another embodiment, the item support member may include a base member and a plurality of transparent rod members extending upward from the base member along a width of the base member and a plurality of transparent protuberances that extend from the base member such that they are positioned below the plurality of transparent rod members. This embodiment of the item support member may function particularly well for supporting bottles being sanitized using the device. All embodiments of the support member may be removable from the enclosure of the device.

The enclosure of the device may be plugged into an AC power source and a transformer may convert the AC to DC for battery charging. After long periods of use, the enclosure and its internal accessories may need to be cleaned with a sanitary cloth or wiper.

The sanitizing device may include means to inform the user about the actual state of operation of the device. It may also have a weight sensor to determine whether an item to be sanitized is contained within the enclosure and a lid closure sensor to determine whether it is safe to turn on the UV light. The device may also accommodate a humidifying sponge or humidifying wick to assist in ozone generation. It may also have an odor or chemical molecule sensor, or both, to determine the sanitizing time required and an ozone level sensor to determine the air cleanness level inside the enclosure to determine when the sanitization is complete. At least one electronic controller may command actions based on the sensory measurements. The device may also allow for vibration of the personal use item contained within the enclosure during its sanitation to ensure that no areas remain shadowed and protected from the electromagnetic radiation during sanitizing.

Some personal use items may be made with plastics or elastomerics which may be sanitized at their surface after 30-90 minutes using the thymine dimer (280 nm) mode of electromagnetic radiation. Some personal use items may be charged inductively. These have built in charged state indicators and do not need to be plugged in. Based on the current used by the inductor, the sanitizer can indicate whether the personal use item is still charging.

A user of the sanitizing device may wish to collect data of odor history and auto-shutdown time. These are indicative to user health and change over time. The controller memory may store, manage and display such data for years and may pass it wired or wirelessly to at least one mobile or stationery computing device for trends and habit monitoring.

The present invention is also directed to a system for sanitizing personal use items that includes at least one control module configured to determine whether the system is in an activated state; at least one power module coupled to the control module and configured to power at least one electromagnetic emitter, at least one user interface coupled to the control module and configured to receive user control inputs, at least one sanitization module that includes the electromagnetic emitter(s), at least one item support having a plurality of members extending from the item support, and at least one enclosure that contains the control module, the power module, the user interface, the sanitization module, and the item support.

The foregoing is a summary and thus contains, by necessity, simplifications, generalizations and omissions of detail; consequently, those skilled in the art will appreciate that the summary is illustrative only and is NOT intended to be in any way limiting. Other aspects, embodiments, features and advantages of the device and/or processes and/or other subject matter described herein will become apparent in the teachings set forth herein.

BRIEF DESCRIPTION OF THE DRAWINGS

Certain embodiments of the present invention are described in detail below with reference to the following drawings, presented in accordance with varied embodiments of the invention.

DETAILED DESCRIPTION OF EXEMPLARY EMBODIMENTS

Figure 1:
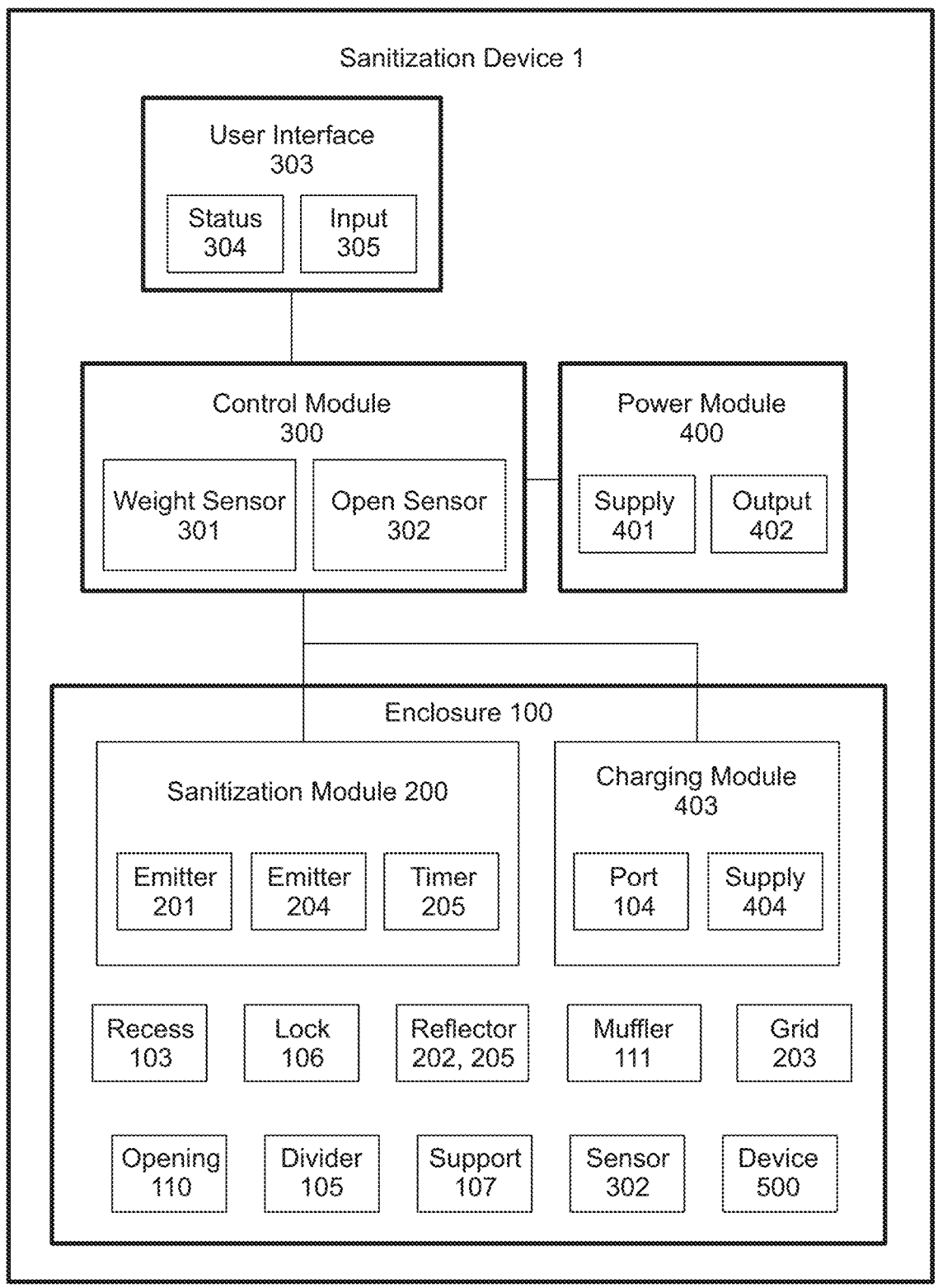
FIG. 1 is a block diagram of one embodiment of the sanitization apparatus.

This application relates generally to storing and sanitizing devices, and, more specifically, to storing, sanitizing, and charging devices with complex shapes. Specific details of certain exemplary embodiments of the invention are set forth in the following description and in FIGS. 1-25 to provide a thorough understanding of such embodiments. The present invention may have additional embodiments, may be practiced without one or more of the details described for any particular described embodiment, or may have any detail described for one particular embodiment practiced with any other detail described for another embodiment.

Importantly, a grouping of inventive aspects in any particular "embodiment" within this detailed description, and/or a grouping of limitations in the claims presented herein, is not intended to be a limiting disclosure of those particular aspects and/or limitations to that particular embodiment and/or claim. The inventive entity presenting this disclosure fully intends that any disclosed aspect of any embodiment in the detailed description and/or any claim limitation ever presented relative to the instant disclosure and/or any continuing application claiming priority from the instant application (e.g. continuation, continuation-in-part, and/or divisional applications) may be practiced with any other disclosed aspect of any embodiment in the detailed description and/or any claim limitation. Claimed combinations which draw from different embodiments and/or originally-presented claims are fully within the possession of the inventive entity at the time the instant disclosure is being filed. Any future claim comprising any combination of limitations, each such limitation being herein disclosed and therefore having support in the original claims or in the specification as originally filed (or that of any continuing application claiming priority from the instant application), is possessed by the inventive entity at present irrespective of whether such combination is described in the instant specification because all such combinations are viewed by the inventive entity as currently operable without undue experimentation given the disclosure herein and therefore that any such future claim would not represent new matter.

Disclosed herein are exemplary embodiments of apparatus, systems, and methods for sanitizing various devices. The disclosed embodiments may provide for charging the device while it is being sanitized. In some embodiments, the device is sanitized by use of electromagnetic radiation. Certain wavelengths of Ultraviolet (UV) or Infrared (IR) radiation may be used to sanitize a device. As used herein, light, radiation, or "sanitizing radiation" refers to any suitable wavelength and/or type of electromagnetic radiation capable of sanitizing a surface, such radiation may include, but is not limited to: type-C ultraviolet radiation (UV-C) comprising wavelengths between 280-100 nm, type B ultraviolet radiation (e.g. UV-B), middle ultraviolet radiation (MUV), far ultraviolet radiation (FUV), ionizing electromagnetic radiation, non-ionizing electromagnetic radiation, a combination of wavelengths and/or electromagnetic radiation types, or the like.

FIG. 1 is a block diagram of one embodiment of a device sanitization apparatus 1. The device sanitization apparatus 1 may comprise an enclosure 100, a sanitization module 200, a control module 300, and a power module 400. The control module may be communicatively coupled to the sanitizing module 200, power module 400, and a user interface 303. The control module 300 may be configured to control the operation of the sanitization module 200 and/or power module 400, which may comprise selectively activating and/or deactivating the sanitization module 200 and/or power module 400.

In some embodiments, the control module 300 may comprise an on/off switch. When a user wishes to sanitize a device 500, he or she moves the switch into the on position, causing power to flow to emitters 201 and 204. When the user is finished sanitizing, he or she moves the switch to the off positon, terminating power to the emitters 201 and 204. In some embodiments, the control module 300 may include a timer 205 that begins timing when the switch is moved into the on position, and that automatically switches the power off when the designated time has elapsed.

In some embodiments, the control module 300 may comprise a weight sensor 301. The weight sensor 301 may comprise one or more scales, such as a spring scale, a strain gauge scale, a balance scale, a microbalance scale, an analytical balance scale, or the like. In some embodiments, the weight sensor 301 may be configured to interface with the control module 300 such that the apparatus 1 will not activate unless a change in weight has been detected, indicating that a device 500 has been placed in or removed from the apparatus 1. In other embodiments, the weight sensor 301 may be configured to interface with the control module 300 such so as to prevent activation of the sanitization apparatus 1 unless a certain weight threshold has been met, indicating that a device 500 is present in the apparatus. In still other embodiments, control module 300 may prevent activation of the device if the weight sensor 300 detects a weight over a certain threshold, indicating that a device 500 that is too large or too heavy for the apparatus is present, or that a user is somehow adding undue weight to the device, perhaps indicating that the device is in fact in the open state, not the closed state.

The control module 300 may further comprise an open sensor 302. Open sensor 302 may be any number of mechanisms indicating that the apparatus 1 is in an open configuration, in which it is undesirable to have the apparatus activated. Open sensor 302 may be an electronic sensor, a gyroscope that detects the position of one or more elements of the enclosure 100, a sensor for detecting the relative position of one or more elements of the enclosure 100, or the like. In some embodiments, open sensor 302 may be disposed in the enclosure, comprising one or more detection mechanisms including, but not limited to: contact switches, conductive switches, magnetic switches, capacitive switches, resistive switches, latches, or the like. In some embodiments, open sensor 302 may have one element in the control module 300, such as a mechanism for converting a physical signal to an electronic indication, and one element in the enclosure 100, configured to detect the state of the enclosure and provide the status to the control module 300.

The control module 300 may further comprise a user interface 303. The user interface 303 may comprise one or more input/output components, such as buttons, switches, displays, and the like. The user interface 303 may comprise a status indicator 304 configured to display and/or communicate status information pertaining to the device sanitization apparatus 1, such as current sanitization status, sanitization time, charge status, charge time, powered-on state, closure state of the enclosure 100, and so on. In some embodiments, the status indicator 304 may comprise one or more visual indicators alone or in combination, such as a Liquid Crystal Display (LCD), one or more light emitters such as Light-Emitting Diodes (LEDs), or the like. The status indicator 304 may comprise one or more acoustic indicators designed to produce sounds or speech to indicate the sanitizing and/or charging status. The acoustic indicator may be a speaker, a vibrator, or any other mechanism configured to generate vibrations or other acoustic signals. The user interface 303 may further comprise an input module 305 configured to receive user input and/or configuration information, such as sanitization time and/or mode parameters, charge settings, and so on. In some embodiments, user interface 303 may be a transponder configured to receive and transmit user control signals from an external device, such as a mobile phone, a smartphone, a computer, a tablet computer, or another electronic communication device. In such embodiments, control of the apparatus 1 could effectively be moved to a user interface on a display device, allowing a user to lock/unlock, activate/deactivate, set the parameters for sanitization, etc., on the apparatus from a remote location. The user interface 303 may be coupled with apparatus 1 via wires, wirelessly, through mobile or wi-fi signals, Bluetooth®, infrared signaling mechanisms, and the like.

The device sanitization apparatus 1 may further comprise an enclosure 100 configured to receive a device 500 via an opening 110. The opening 110 may comprise a clamshell configuration, a tray, or the like. In preferred embodiments, the opening 110 is created when upper member 101 is lifted from lower member 102 (see FIG. 2) as in a clamshell configuration. The enclosure 100 may allow a closed configuration and an open configuration. As described above, in the closed configuration, the enclosure 100 may be sealed with respect to electromagnetic radiation, such that electromagnetic radiation emitted therein (e.g., by emitters 201 and 204 of the sanitization module 200) is not emitted outside of the enclosure 100. The enclosure 100 may include an open sensor 302 configured to detect whether the enclosure 100 is in the closed configuration and communicate the status to control module 300. The open sensor 302 may be configured to communicate the closure status of the enclosure 100 to the control module 300. The control module 300 may be configured to deactivate the sanitization module 200 when the enclosure 100 is not in the closed configuration. As described above, the open sensor 302 may comprise one or more detection mechanisms, such as switches, latches, or the like.

Enclosure 100 may further include a lock 106. Lock 106 may be any manner of lock, including but not limited to a combination lock, a key lock, a biometric lock, an electronic lock (for instance, an RFID receiver), etc. Lock 106 may be used in conjunction with sensor 302 to establish that the apparatus 1 is in a state wherein activation of the sanitization cycle can begin. Lock 106 may be used individually to prevent unauthorized access to the apparatus 1, and, therefore, to any device 500 stored within. Lock 106 may further be configured to prevent access after a certain number of attempts, thereafter requiring an override code from an authorized user.

The sanitization module 200 may be configured to emit electromagnetic radiation into an interior of the enclosure 100. The electromagnetic radiation may be configured to irradiate the surface of the device 500 within the enclosure 100. The sanitization module 200 may be configured to emit electromagnetic radiation at one or more wavelengths, which, as described above, may be configured to kill, and/or render harmless, organisms on the surface of the device 500 (e.g., bacteria). In some embodiments, the sanitization module 200 is configured to emit a single wavelength of electromagnetic radiation. In other embodiments, the sanitization module 200 is configured to emit a broad spectrum of sanitizing electromagnetic radiation. The sanitization module 200 may be configured to emit multiple discrete wavelengths or multiple narrow spectrums of electromagnetic radiation. In some embodiments, the sanitization module 200 is configured to emit electromagnetic radiation at wavelengths between 240 nm and 280 nm, which may disrupt the chemical bonds of DNA and RNA, thereby killing microorganisms. Radiation emitted at these wavelengths is also known to break down organic molecules and carbon-based molecules. In some embodiments, a wavelength of the electromagnetic radiation is selected to be suitable for breaking down particles of grease or skin oil. In some embodiments, the emitted wavelengths of electromagnetic radiation are preselected. In other embodiments the emitted wavelengths are selected by the user, for example by the user selecting a set of wavelengths or indicating a choice between a plurality of preset combinations of wavelengths via the user interface 303.

The sanitization module 200 may comprise an emitter 201 configured to emit electromagnetic radiation of an appropriate wavelength and/or intensity to sanitize the device 500, as described above. The emitter 201 may be located in a suitable position within the enclosure 100 so that the entire surface of the device 500 is exposed to the electromagnetic radiation. In some embodiments, the sanitization module 200 may comprise a plurality of emitters 201 configured to irradiate the device 500 from different locations, angles, and/or positions within the enclosure 100.

In some embodiments, a single emitter 201 is used, and electromagnetic radiation emitted therefrom is reflective, refracted, and/or diffused within the enclosure 100 (by an inner surface of the enclosure 100 or by a reflector 202). In some embodiments, one or more emitters 201 are located directly above or below the device and electromagnetic radiation is propagated through the interior portion by means of reflective and/or refractive surfaces. In other embodiments, one or more emitters 201 are disposed at the side of the device 500 and electromagnetic radiation is propagated through the enclosure 100 by means of reflective and/or refractive surfaces. In other embodiments, one emitter 201 is disposed above a device 500, one emitter 204 is disposed below a device, and a plurality of reflectors 202, 205 work in conjunction with a reflective grid 203 to ensure that the entire surface is exposed, including in recesses formed by curves, angles, holes, ports, etc., of complex shapes. In still other embodiments, a plurality of emitters are located throughout the enclosure 100. In some embodiments, the emitters may be permanently coupled with the enclosure 100. In other embodiments, the emitters may be removable and replaceable by a user.

Reflectors 202 and 205 may be a reflective material disposed on the top and/or bottom of the enclosure 100. In some embodiments, the reflective material may be substantially smooth, following the shape of the top of the enclosure and reflecting light accordingly. In other embodiments, reflectors 202 and 205 may include geometric structure, such as ridges and valleys, to alter the natural reflection of the electromagnetic radiation. This may allow the sanitizing radiation to reach more areas of the device.

The emitter 201 may comprise any suitable electromagnetic radiation source, including, but not limited to, a light emitting diode (LED), a laser, an electric arc discharge, a gas-discharge lamp, a fluorescent lamp, or the like. In some embodiments, the emitter 201 is configured to be compact to minimize the size requirements of the apparatus 100. In another embodiment, a larger dimensioned emitter(s) 201 may be used.

The emitter 201 may further comprise one or more lenses for distributing, focusing, spreading, or otherwise directing electromagnetic radiation emitted thereby to particular portions of the interior of the enclosure 100. The emitter 201 may further comprise one or more filters capable of blocking unwanted portions and/or wavelengths of electromagnetic radiation. As a non-limiting example, a low-pressure mercury-vapor lamp emits electromagnetic radiation at peak wavelengths of approximately 184 nm and 254 nm. While both wavelengths can be used to sanitize a device, electromagnetic radiation of 184 nm will also produce ozone, which may be undesirable. Accordingly, the low-pressure mercury-vapor lamp may be used in conjunction with a filter designed to block 184 nm electromagnetic radiation while passing through 254 nm electromagnetic radiation.

Sanitization module 200 may further include a timer 205. Timer 205 may be configured to activate the apparatus 1 at a particular time of day, to prevent activation during a particular time of day, to set the length of time for activation, to prevent activation until a particular amount of time has passed since the last cycle, and so on. In some embodiments, timer 205 may be user configurable, allowing a user to set the length of time for sanitization, for example, based on a manufacturer's instruction. In other embodiments, timer 205 may include one or more timer presets, wherein the timer begins upon activation or deactivation of the device.

Enclosure 100 may comprise an interior portion or region configured to receive the device 500. An inner surface of the enclosure 100 may be configured to direct electromagnetic radiation to the device 500. Accordingly, in some embodiments, portions of the interior surface of the enclosure 100 may comprise reflective material configured to reflect emitted electromagnetic radiation to the device 500 such that the entire surface of the device 500 is exposed thereto. In some embodiments, substantially all of the surface of the enclosure 100 is configured to reflect electromagnetic radiation. Alternatively, only certain portions of the surface may be comprised of reflective material (e.g., portions that face the device 500). In embodiments where reflective material is used, the device 500 may be exposed to reflected sanitizing electromagnetic radiation that reaches the device 500 at oblique angles to minimize shadowing on the surface of the device 500. The shadowing may be caused, for example, by particles on the surface of the device 500, by features, such as seams or buttons, on the surface of the device 500, or by scratches or other flaws in the surface of the device 500. In yet another embodiment, no reflective material is used, but rather the emitters 201 of the sanitization module 200 are arranged so that the entire surface of the device 110 is directly exposed to electromagnetic radiation.

Figure 5:
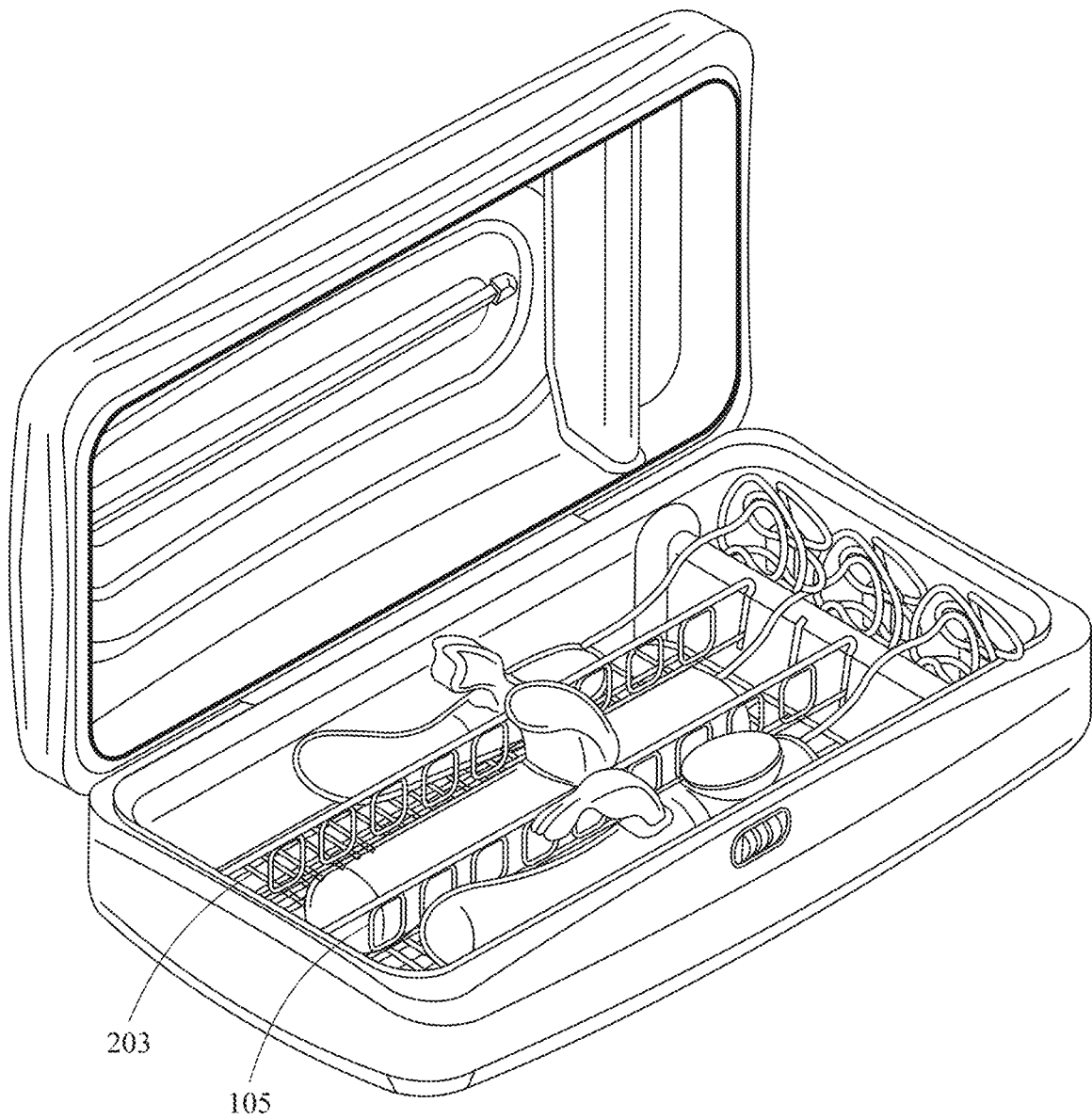
FIG. 5 is a front isometric view of one embodiment of the sanitization apparatus with devices to be sanitized in place.

In a preferred embodiment, a reflective grid 203 is disposed within enclosure 100 such that device 500 is placed onto, above, and/or below the grid. The grid 203 is configured to reflect the electromagnetic radiation at angles that would otherwise be difficult to achieve using standard configurations, even including configurations with multiple sources. For instance, FIG. 5 shows three complex shaped devices 500 disposed within the apparatus 1. Even with a plurality of sources disposed throughout the apparatus 1, the electromagnetic radiation may not reach the entire surface of each of the complex devices 500. However, grid 203 is configured to change the reflective angle of the electromagnetic radiation, allowing the radiation to reach the entire surface of each device 500. In some embodiments, grid 203 may be comprised of a simple straight grid, where each unit of the grid is substantially rectangular. In other embodiments, the grid 203 may include curved elements, or elements of other shapes, to further alter the reflective angle of the radiation. In some embodiments, the grid 203 may be comprised of a reflective rod that is substantially rectangular or triangular in cross section, giving the grid specific angles of reflection. In other embodiments, the grid 203 may be comprised of a reflective rod that is substantially convex or concave in cross section, giving the grid a wide range of reflective angles. In some embodiments, grid 203 may be permanently coupled with enclosure 100. In other embodiments, grid 203 may be removable, replaceable, and/or reconfigurable.

In some embodiments, device sanitization apparatus 1 may comprise a device support 107 that is configured to maintain the device 500 at a particular orientation and/or position within the enclosure 100. The device support 107 may be configured to maintain the device 500 in an orientation and/or position configured to allow electromagnetic radiation emitted by the emitter 201 irradiate substantially the entire surface of the device 500. In some embodiments, the device support 107 may be transparent or substantially transparent to the electromagnetic radiation emitted by the emitter 201. Accordingly, the device support 107 may be comprised of electromagnetic transparent materials. The support member may be made of glass, plastic, polymer, ceramic, or other suitable materials sufficiently transparent to the electromagnetic radiation emitted by the sanitization module 200. In some embodiments, the emitter 201 may be placed below the device support 107 such that sanitizing electromagnetic radiation is emitted through the device support 107 onto the surface of the device 500. The intensity of the emitters 201 located below the device support 107 may be increased relative to other emitters 201 to compensate for partial absorption of the sanitizing electromagnetic radiation by the device support 107. In some embodiments, the apparatus 1 may include two supports 107, one in each half of a clamshell configuration, for example, such that the device 500 is held in position relative to the entirety of the apparatus. Support 107 may include, or may be used in conjunction with, divider 105. This is especially useful for sanitization of multiple devices 500, as in FIG. 5, or for sanitization of a single, smaller device, in order to prevent movement of the device. Dividers 105 may also be useful during travel for securing device 500, alone or in combination with support 107, so that neither the device nor the apparatus 1 are damaged during transit. In some embodiment, the device support 107 may be configured to filter electromagnetic radiation and/or otherwise modify electromagnetic radiation emitted by the electromagnetic emitter 201.

In some embodiments, the device support 107 may comprise a flat support member (e.g., plate) configured to hold the device 500 in a horizontal orientation. In some embodiments, a connector of the power module 400 may be rigidly attached to the device 500 such that the device 500 is secured within the enclosure 100. Alternatively, or in addition, the device support 107 may comprise a textured surface capable of preventing, or minimizing, movement of the device 500. In some embodiments, the device support 107 further comprises raised members that prevent the device from sliding off of the device support 107. The raised members may be transparent to the sanitizing electromagnetic radiation. In another embodiment, the raised members are reflective to the sanitizing electromagnetic radiation.

In some embodiments, the enclosure 100 may comprise an acoustic muffler 111 configured to prevent transmission of acoustic waves outside the enclosure. The muffler 111 may, therefore, prevent a user from hearing when a device 500 alerts, buzzes, vibrates, rings, or otherwise emits a sound. This may be especially useful when the device 500 is a child's toy in order to prevent the child from hearing the toy and demanding it before the sanitization cycle has completed. It may also be useful when the device 500 is an adult toy in order to prevent individuals other than the user from hearing if the device is inadvertently activated. For example, if the device 500 is a vibrator, and the vibrator is inadvertently activated during travel, muffler 111 may prevent fellow passengers or transit officials from identifying the nature of the device by its sound.

The power module 400 may be configured to charge or recharge the device 500. The power module 400 may comprise a supply means 401 to supply electrical power to the apparatus 1. The connector may be a physical connector that plugs into the apparatus 1, such as a Universal Serial Bus (USB) connector, mini-USB connector, micro-USB connector, 30-pin connector, a proprietary connector, and AC/DC convertor, or the like. Supply 401 may be a removable and/or rechargeable battery, such as a lithium ion battery, standard batteries such as AAA sized batteries, or an external power pack.

Alternatively, or in addition, the power module 400 may comprise an output 402 configured to power or charge a device 500 while the device is coupled with apparatus 1. In some embodiments, output 402 may be a physical connector that plugs into the apparatus 1, such as a Universal Serial Bus (USB) connector, mini-USB connector, micro-USB connector, 30-pin connector, a proprietary connector, and AC/DC convertor, or the like, and then couples with charging module 403 via supply 404. In other embodiments, output 402 may be an inductive coil to transfer power wirelessly to the device 500. In some embodiments the connector of the power module 400 may be further configured to act as a docking connector for the device 500 (e.g., communicate data between the device 500 and a computing device, hub, or the like). In some embodiments, the apparatus 1 may include ports 104 that allow a cord configured for use with device 500 to pass through enclosure 100. In such embodiments, port 104 may include a gasket, sheath, casing, sleeve, etc., that allows the cord of device 500 to pass through enclosure 100 without permitting passage of the electromagnetic radiation. Alternatively, the power module 400 may comprise an intermediary cable or cord with an exterior connector for connecting to a third-party charger and an interior connector. In some embodiments, enclosure 100 may include a recess 103 for storing extra batteries, extra cord lengths, etc. Recess 103 may be configured to be light-tight, which is to say that the recess may be part of the enclosure but protected from the electromagnetic radiation. In other embodiments, recess 103 may be exposed to the radiation, allowing cords or other accessories stored in the recess to be sanitized at the same time as the device 500.

In some embodiments, the device sanitizing apparatus 100 may be configured to act as an end node of the data connection or may be configured to act as an intermediary node (hub) used to establish a data connection between the device and another, external computing device. In some embodiments the power module 400 may comprise a removable adaptor capable of connecting to various different types of connectors and/or devices. In some embodiments the connector of the power module 400 is extendable so that the device 500 can be positioned at different locations and/or orientations within the enclosure 100.

As disclosed above, the control module 300 may be configured to control the charging and/or sanitizing operations of the apparatus 100. The control module 300 may comprise a microprocessor, an application-specific integrated circuit (ASIC), an integrated circuit, programmable logical array (PLA), or the like. In some embodiments the control module 300 comprises a timer module and/or process configured to track time information pertaining to the operation of the sanitizing module. The control module 300 references the timing information to determine when to cause the sanitization module 200 to stop emitting electromagnetic radiation. The control module 300 may, therefore, control the exposure time of the device 500. In some embodiments, the control module 300 automatically deactivates the sanitization module 200 after a predetermined irradiation time. In some embodiments, the exposure time may be determined from user input (received via the user interface 303). In another embodiment, the exposure time is automatically calculated by the control module 300; the exposure time may be selected according the intensity, wavelength, and/or type of electromagnetic radiation emitted by the sanitization module 200. In some embodiments, the amount of exposure time may vary according to the contamination level of the device 500.

As disclosed above, the control module 300 may be coupled to the open sensor 302 to determine whether the enclosure 100 is in a closed configuration. The control module 300 may be configured to deactivate the sanitization module 200 while the enclosure 100 is not in the closed configuration. The control module 300 may be further configured to monitor the closure status of the enclosure 100 during operation of the sanitization module 200 (by use of the open sensor 302), and may interrupt sanitizing operations in response to determining that the enclosure 100 is no longer in the closed configuration. In some embodiments, the control module 300 may be configured to continue a sanitizing cycle (e.g., re-activate the sanitization module 200, but not reset a timer associated with the cycle) in response to closing the enclosure 100. In some embodiments, the sanitizing cycle may be configured to continue the sanitizing cycle if the enclosure 100 is closed within a time threshold; otherwise, the control module 300 may be configured to restart the sanitizing cycle.

In some embodiments the control module 300 is configured to automatically activate the sanitization module 200 in response to detecting a device 500 within the enclosure 100. In some embodiments the control module 300 determines that a device 500 is present within the enclosure 100 by determining whether a device 500 is connected to the power module 400. In some embodiments, the apparatus 100 comprises one or more sensors configured to determine whether a device 500 is present within the enclosure 100. Such sensors may include, but are not limited to, optical sensors, weight sensors, capacitive sensors, resistive sensors, pressure sensors, mechanical switches, or the like.

The control module 300 may be configured to periodically perform self-sanitization operations. Accordingly, in some embodiments, the control module 300 may be configured to automatically activate the sanitization module 200 when the enclosure 100 is closed, regardless of whether the device 500 is present within the enclosure 100. The self-sanitization cycle may ensure that the enclosure 100 is free of bacteria and/or other contaminants in areas obscured by the device 500. In some embodiments, a self-sanitization process may be invoked manually through the user interface 303.

The apparatus 100 may further comprise one or more latching and/or securing mechanisms configured to maintain the enclosure 100 in a closed configuration. The mechanisms may be further configured to prevent electromagnetic radiation from escaping the enclosure 100. In some embodiments, the enclosure 100 may comprise a pair of magnets configured to secure two halves of the enclosure 100 to one another. In some embodiments, the enclosure 100 may comprise a spring in a hinge that applies a closing force to thereto. In some embodiments, the enclosure 100 comprises a bi-stable spring, or other suitable mechanism, where one stable state corresponds to a closed configuration and the other stable state corresponds to an open position. In some embodiments the latching mechanism is integrated with the open sensor 302 for determining whether the enclosure 100 is in a closed configuration. In some embodiments, the latching mechanism may be integrated with lock 106. For example, in some embodiments, lock 106 may serve as the latching mechanism. In other embodiments, lock 106 may activate automatically upon latching of the two halves of the enclosure.

In some embodiments, the enclosure 100 may comprise an electromagnetic radiation seal configured to prevent leakage of electromagnetic radiation. The radiation seal may comprise a gasket, and/or lips formed at the opening 110 of the enclosure 100. In some embodiments, the electromagnetic radiation seal(s) may comprise material configured to absorb electromagnetic radiation. Portions of the electromagnetic radiation seal(s) may be formed from reflective materials configured to reflect electromagnetic radiation back into the enclosure 100.

Figure 2:
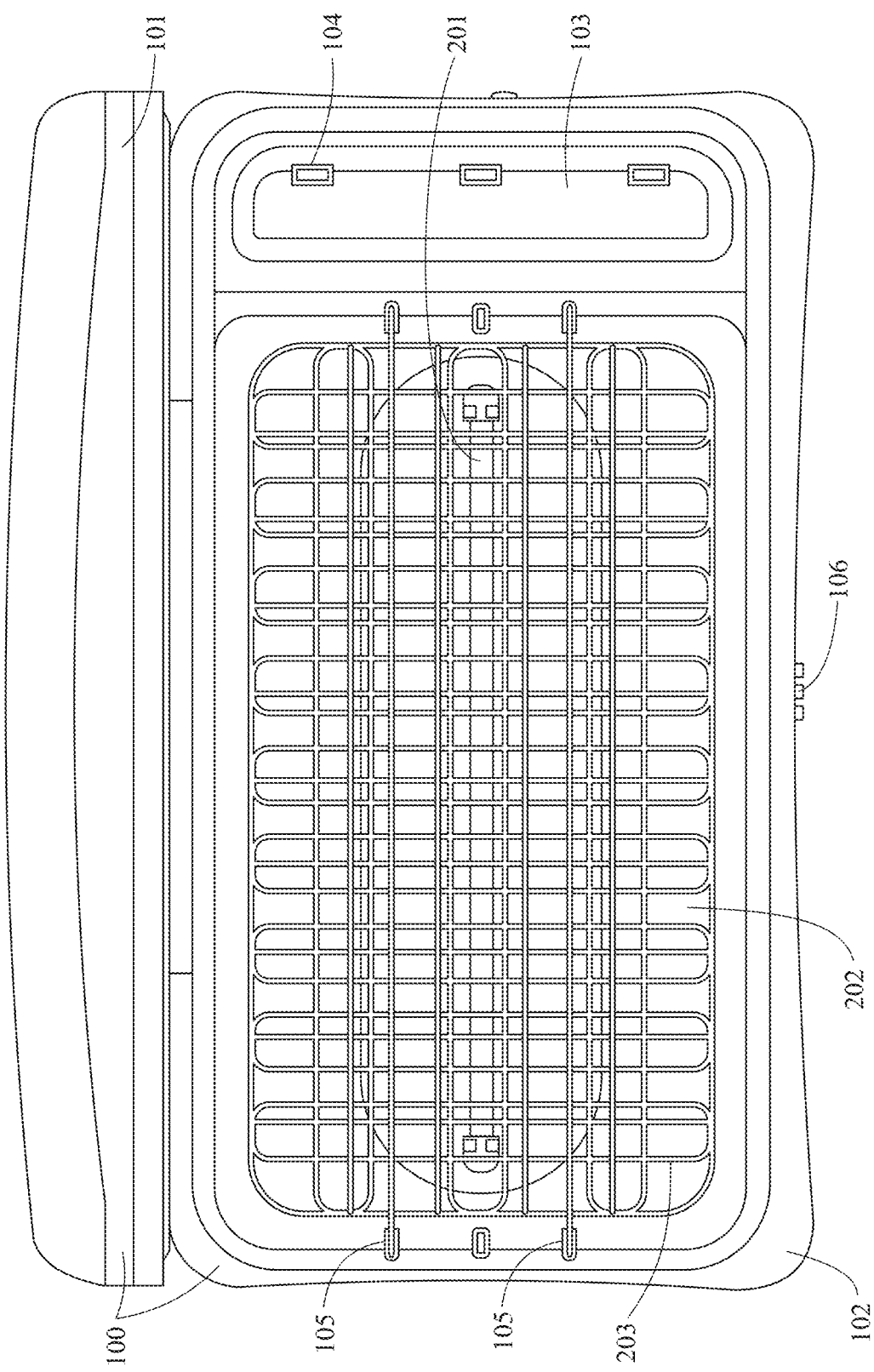
FIG. 2 is a top view of one embodiment of the sanitization apparatus in an open configuration.

FIG. 2 is a top view of one embodiment of the sanitization apparatus in an open configuration. Enclosure 100 is shown comprised of top 101 and bottom 102. Bottom 102 includes recess 103, in which ports 104 are depicted. As above, ports 104 may be pass-through ports, allowing a user to connect a charging cable to device 500, or they may be active ports, allowing a user to charge a device via the power supply 401 of the apparatus 1. Enclosure 100 may also include dividers 105. Here the dividers 105 are depicted as two dividers distributed at approximately ⅓ and ⅔ the width of the enclosure 101, respectively. However, in some embodiments, there may be only one divider 105, and there may be a plurality of dividers 105. In some embodiments, dividers 105 may be fixed, and in other embodiments they may be removable or configurable, allowing a user to place devices of different widths within enclosure 100. In some embodiments, dividers 105 may include or be comprised of additional emitters. FIG. 2 also depicts lock 106, here as a combination lock disposed on the outside of the apparatus 1, configured to prevent the opening of enclosure 100 when activated.

As depicted in FIG. 2, sanitization module 200 includes emitter 201 in the bottom portion 102 of enclosure 100. Emitter 201 is located above the bottom reflector 202 and below reflective grid 203. Though not depicted in FIG. 2 (in part because it may be transparent), support 107 may be disposed above grid 203 in order to secure a device 500 in a particular location.

Although not depicted in FIG. 2, the apparatus 1 may further comprise a control module, power module, sanitization module, charging module, user interface, and/or other modules as described herein.

Figure 3:
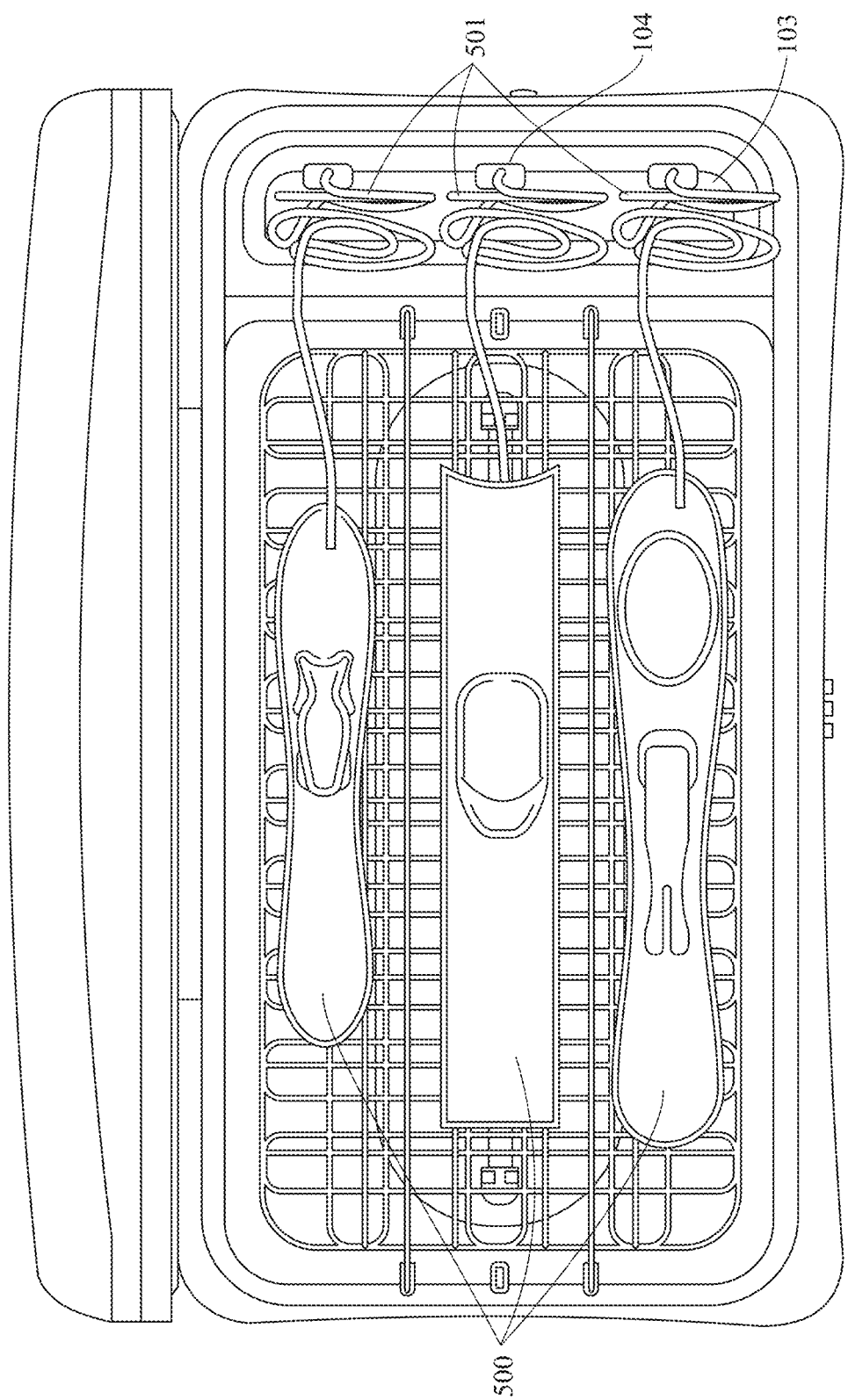
FIG. 3 is a top view of one embodiment of the sanitization apparatus with devices to be sanitized in place.

FIG. 3 is a top view of one embodiment of the sanitization apparatus with devices to be sanitized in place. FIG. 3 shows three devices 500 in place in the sanitization apparatus 1. More specifically, FIG. 3 shows that cords 501 are disposed within recess 103, allowing the unit to close without damaging the cords or allowing light to pass through. As depicted, cords 501 are plugged into ports 104, allowing apparatus 1 to serve as a power source for the devices 500. As disclosed above, this is but one embodiment of the apparatus 1.

Figure 4:
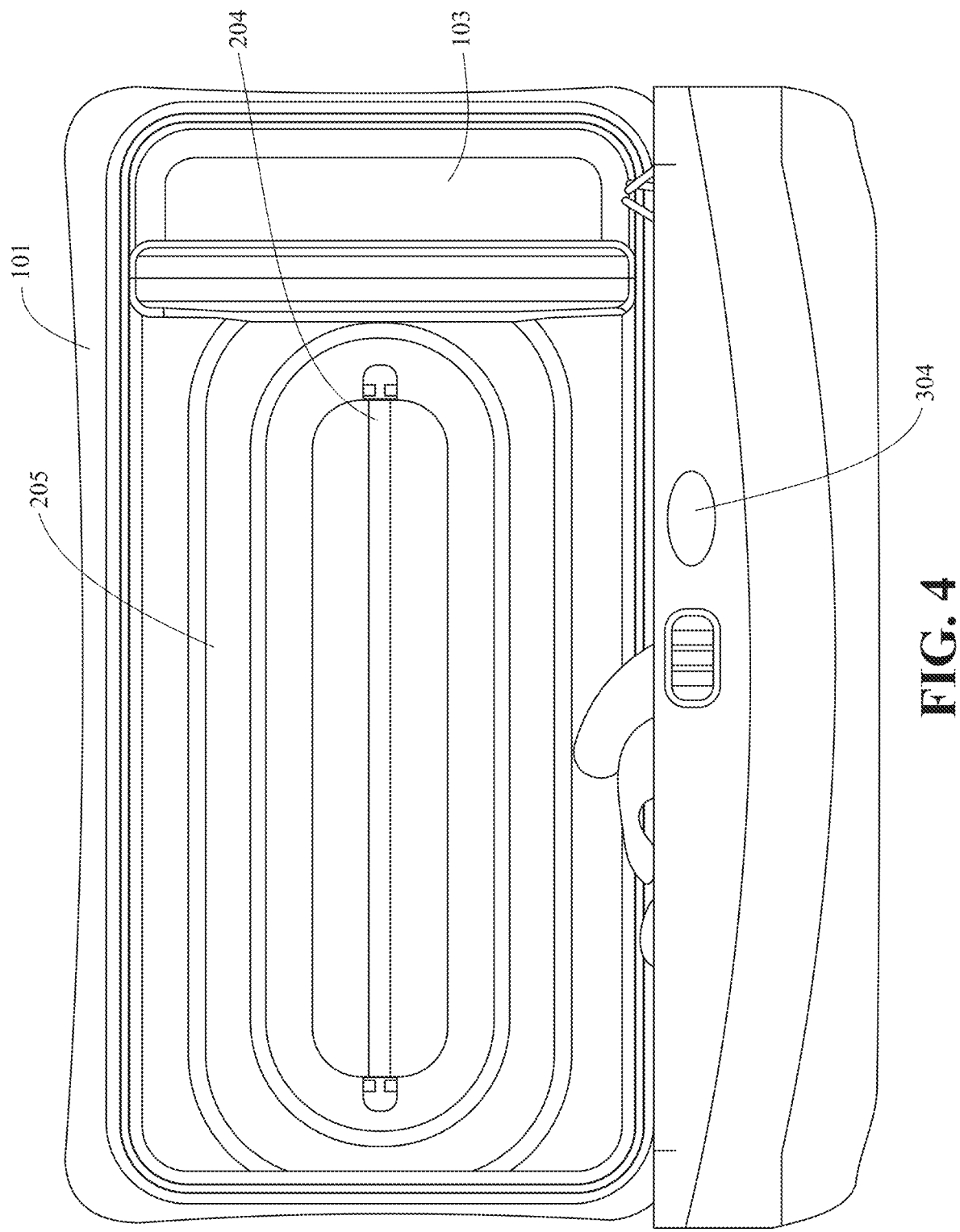
FIG. 4 is a front view of one embodiment of the sanitization apparatus in an open configuration.

FIG. 4 is a front view of one embodiment of the sanitization apparatus in an open configuration. FIG. 4 depicts an embodiment wherein a second emitter 204 is located in the top portion 101 of the enclosure 100. As shown, emitter 204 is a long light emitting tube disposed lengthwise within the enclosure 100. However, as above, this is but one embodiment, and the emitter 204 could be many configurations of emitting devices configured to radiate sterilizing wavelengths. Surrounding emitter 204 is reflector 205, which helps reflect and refract the light such that it reaches all areas within the enclosure 100, including devices 500 and grid 203 (not depicted, see FIG. 2). Disposed on the front of the apparatus 1 is status indicator 304, which, as disclosed above, may indicate a plurality of statuses associated with the device, including but not limited to status of sanitization cycle, power status, lock status, etc. While depicted on the front of the apparatus near the lock 106, it should be understood that the status indicator may be located anywhere on the body of the apparatus. In some embodiments, the status indicator may not be located on the apparatus itself, but may instead be presented on a user dashboard on a display device associated with the apparatus, as disclosed above.

FIG. 5 is a front isometric view of one embodiment of the sanitization apparatus with devices to be sanitized in place. In particular, FIG. 5 depicts three devices 500 in place in the apparatus 1, with divider 105 in place between each device. In some embodiments, divider 105 may be substantially solid. In further embodiments, divider 105 may be substantially transparent or translucent, or may be transparent or translucent to the electromagnetic radiation emitted by emitters 201 and 204. In other embodiments, divider 105 may be substantially comprised of hollow elements, such as rims and structural supports, leaving a large area uninterrupted by the material. In such embodiments, dividers 105 may be substantially similar to grid 203, both in construction and material, not only allowing transmission of nearly all of the electromagnetic radiation, but, in some embodiments, even aiding in the reflective and refractive properties of grid 203.

Figure 6:
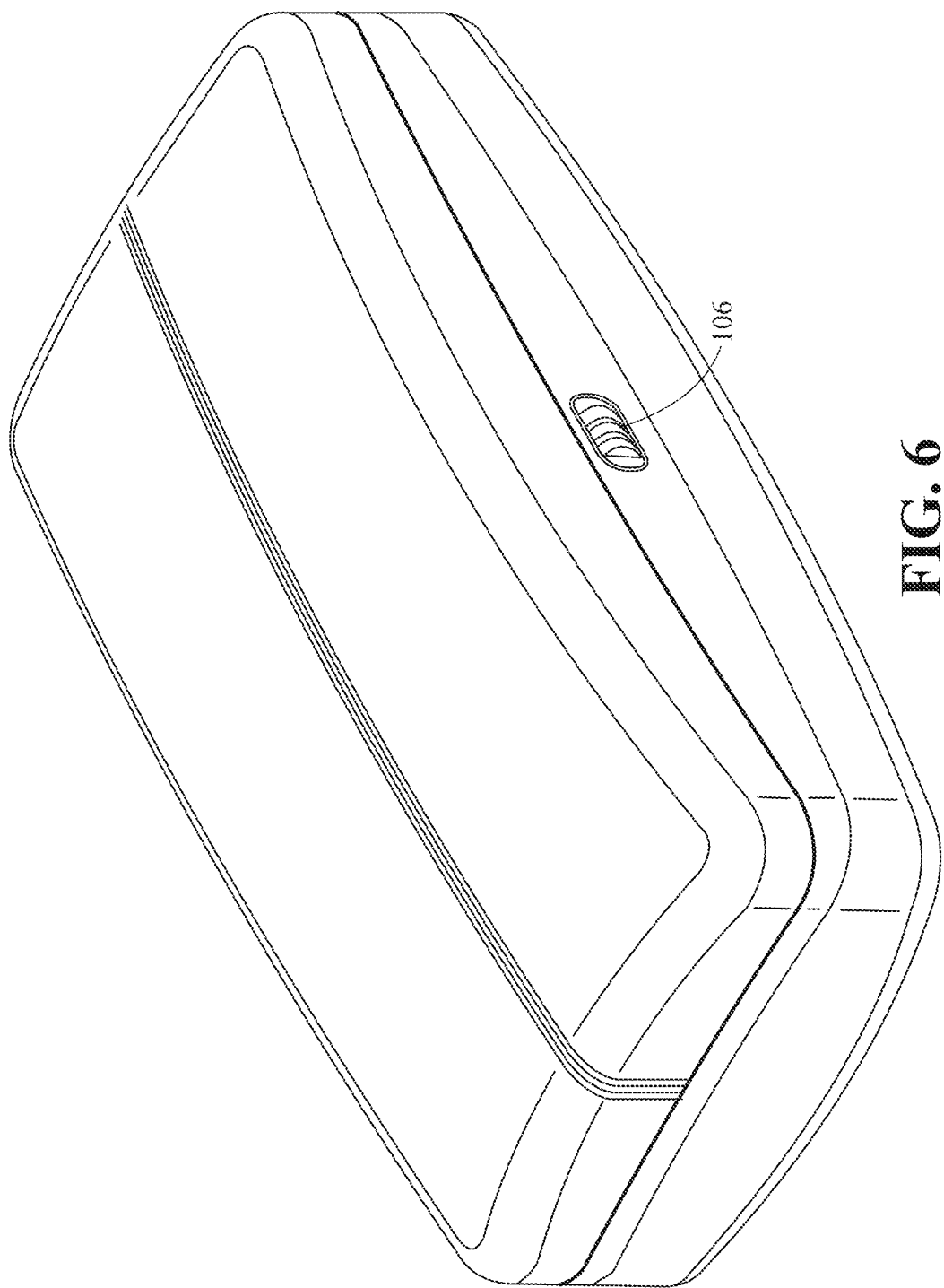
FIG. 6 is a front isometric view of one embodiment of the sanitization apparatus in a closed configuration.

FIG. 6 is a front isometric view of one embodiment of the sanitization apparatus in a closed configuration. Lock 106 is shown on the front of the apparatus 1, allowing a user to engage or disengage the lock as he or she is opening or closing the apparatus. While a combination lock is depicted, as disclosed above, the lock 106 may be a number of different locks according to the user or manufacturer needs. In some embodiments, the lock 106 may be a fingerprint reader configured to send an indication of an authorized or unauthorized attempted access to control module 300, which would then lock or unlock the apparatus accordingly. In embodiments wherein the apparatus is controllable via a user device such as a smartphone, lock 106 may be configured to receive a lock or unlock signal from the user device. In further embodiments, the lock 106 may be configured to be overridden with a signal from the user device, preventing someone from guessing the combination, for example, or allowing a trusted person to open the apparatus when the owner is unavailable to unlock it.

Figure 7:
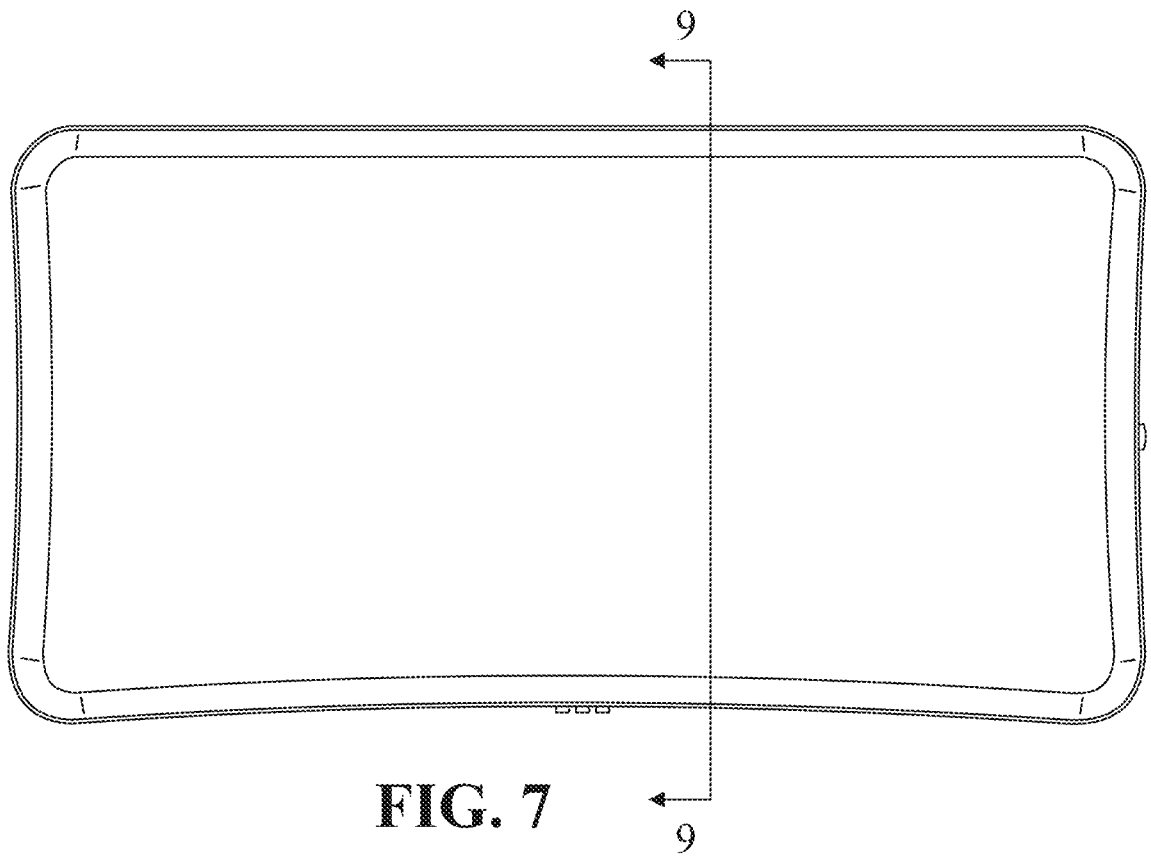
FIG. 7 is a top view of one embodiment of the sanitization apparatus in a closed configuration.
Figure 8:
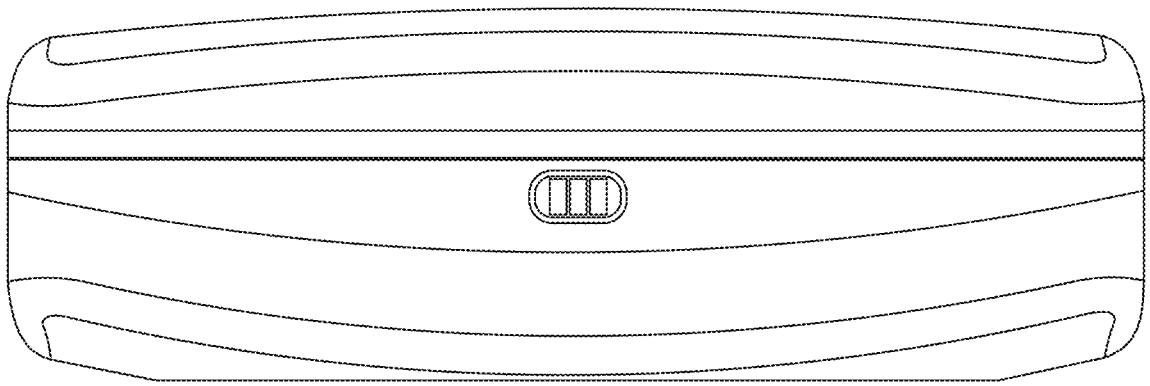
FIG. 8 is a front view of one embodiment of the sanitization apparatus in a closed configuration.
Figure 9:
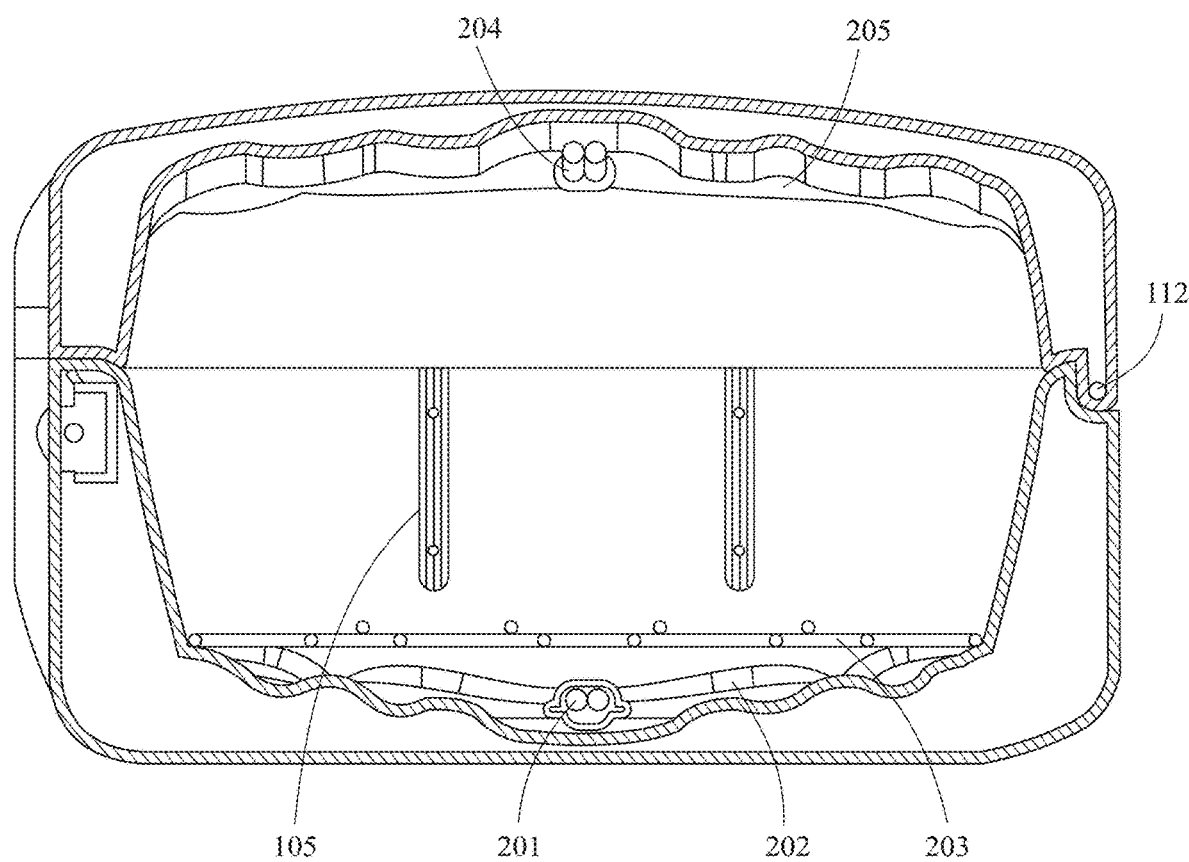
FIG. 9 is a cross-sectional view of one embodiment of the sanitization apparatus.

FIG. 7 is a top view of one embodiment of the sanitization apparatus in a closed configuration, and FIG. 8 is a front view of one embodiment of the sanitization apparatus in a closed configuration. From FIG. 7 comes FIG. 9, a cross-sectional view of one embodiment of the sanitization apparatus. FIG. 7 shows that, when closed, the apparatus forms a light-tight enclosure. FIG. 7 also depicts grid 203 disposed above reflector 202 and emitter 201. Not depicted is support 107, which may be above grid 203, below it, or, in some embodiments, coupled with grid 203. FIG. 9 also depicts dividers 105, which may also be separate or coupled with support 107. In the upper portion 101 of enclosure 100, second emitter 204 and second reflector 205 are disposed such that devices 500 are exposed to radiation from both top and bottom. In combination with the reflectors and grid 203, this configuration should allow maximum exposure of the electromagnetic radiation over the surface of the devices.

FIG. 9 also shows hinge 112, which is only present in clamshell configurations of apparatus 1. In such embodiments, hinge 112 serves as a point about which top portion 101 of enclosure 100 can rotate, allowing access to the inside of the apparatus. In some embodiments, hinge 112 may also serve as a conduit to allow cords or other items to pass from one side of the apparatus to the other safely.

Figure 10:
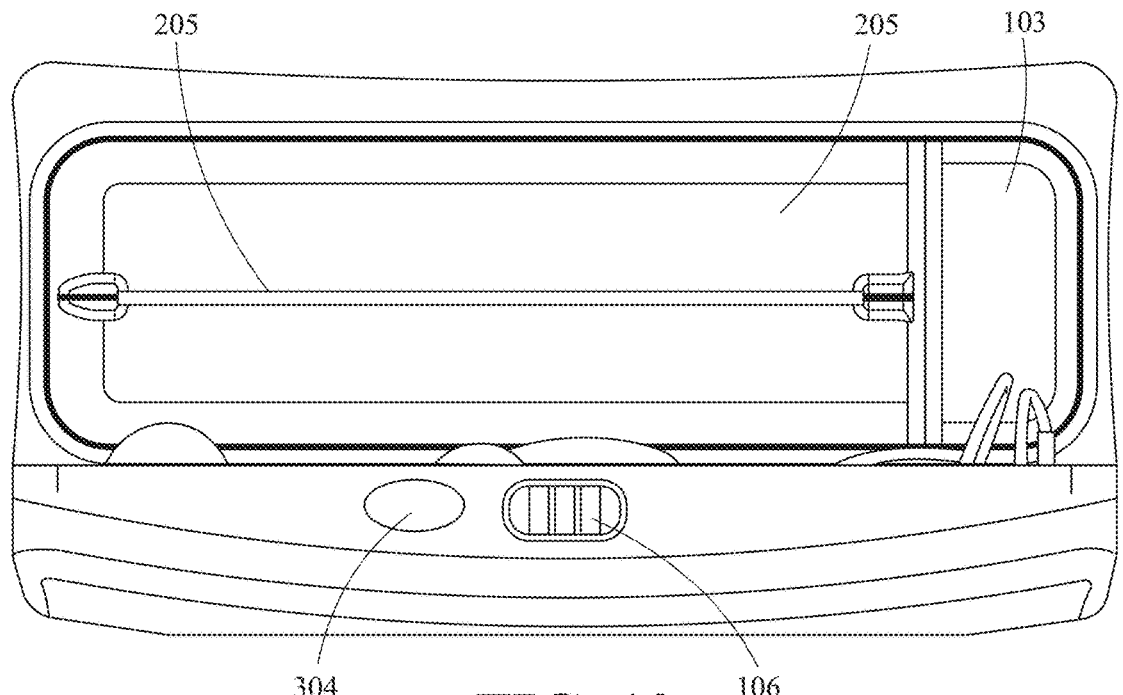
FIG. 10 is a front view of a different embodiment of the sanitization apparatus in an open configuration.
Figure 11:
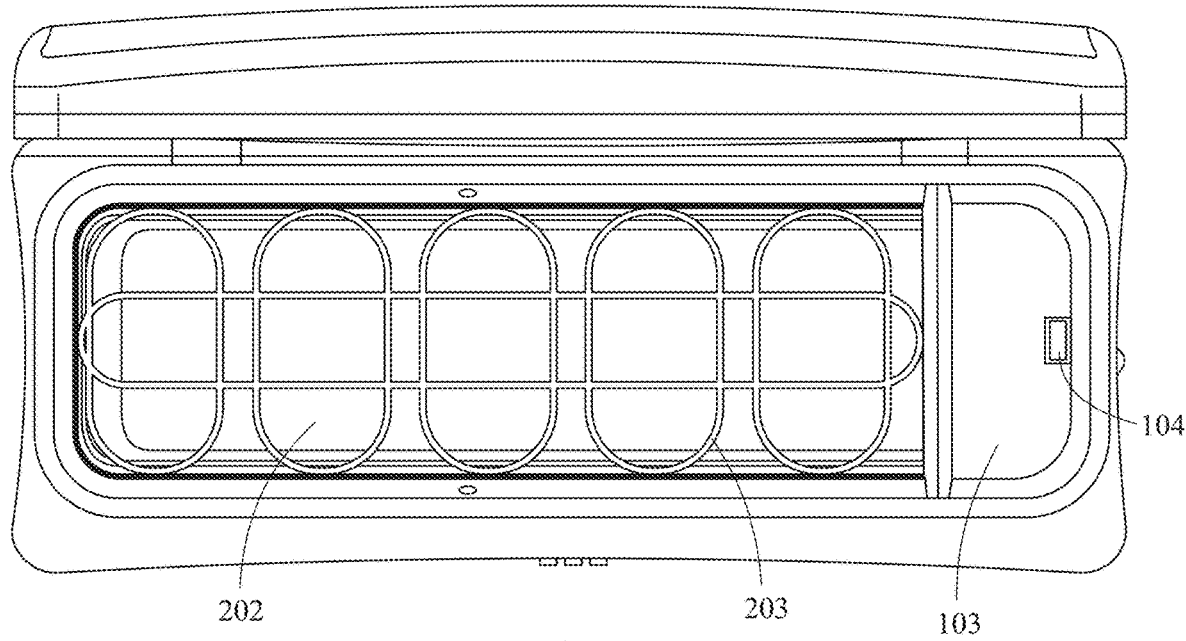
FIG. 11 is a top view of one embodiment of the sanitization apparatus in an open configuration.

FIG. 10 and FIG. 11 are front and top views, respectively, of another embodiment of the sanitization apparatus 1. This embodiment is smaller, configured to hold only one device 500 or a plurality of much smaller devices, such as children's toys. Though smaller, this embodiment still contains many of the same features as the first embodiment disclosed, such as recess 103 with port 104, lock 106, upper emitter 204 and reflector 205, lower reflector 202 and grid 203. While this embodiment is depicted here as having only upper emitter 204, it may also have lower emitter 201. This depiction is exemplary only and is not to be construed as limiting. Disposed on the front of the apparatus 1 is status indicator 304, which, as disclosed above, may indicate a plurality of statuses associated with the device, including but not limited to status of sanitization cycle, power status, lock status, etc. While depicted on the front of the apparatus near the lock 106, it should be understood that the status indicator may be located anywhere on the body of the apparatus. In some embodiments, the status indicator may not be located on the apparatus itself, but may instead be presented on a user dashboard on a display device associated with the apparatus, as disclosed above.

Figure 12:
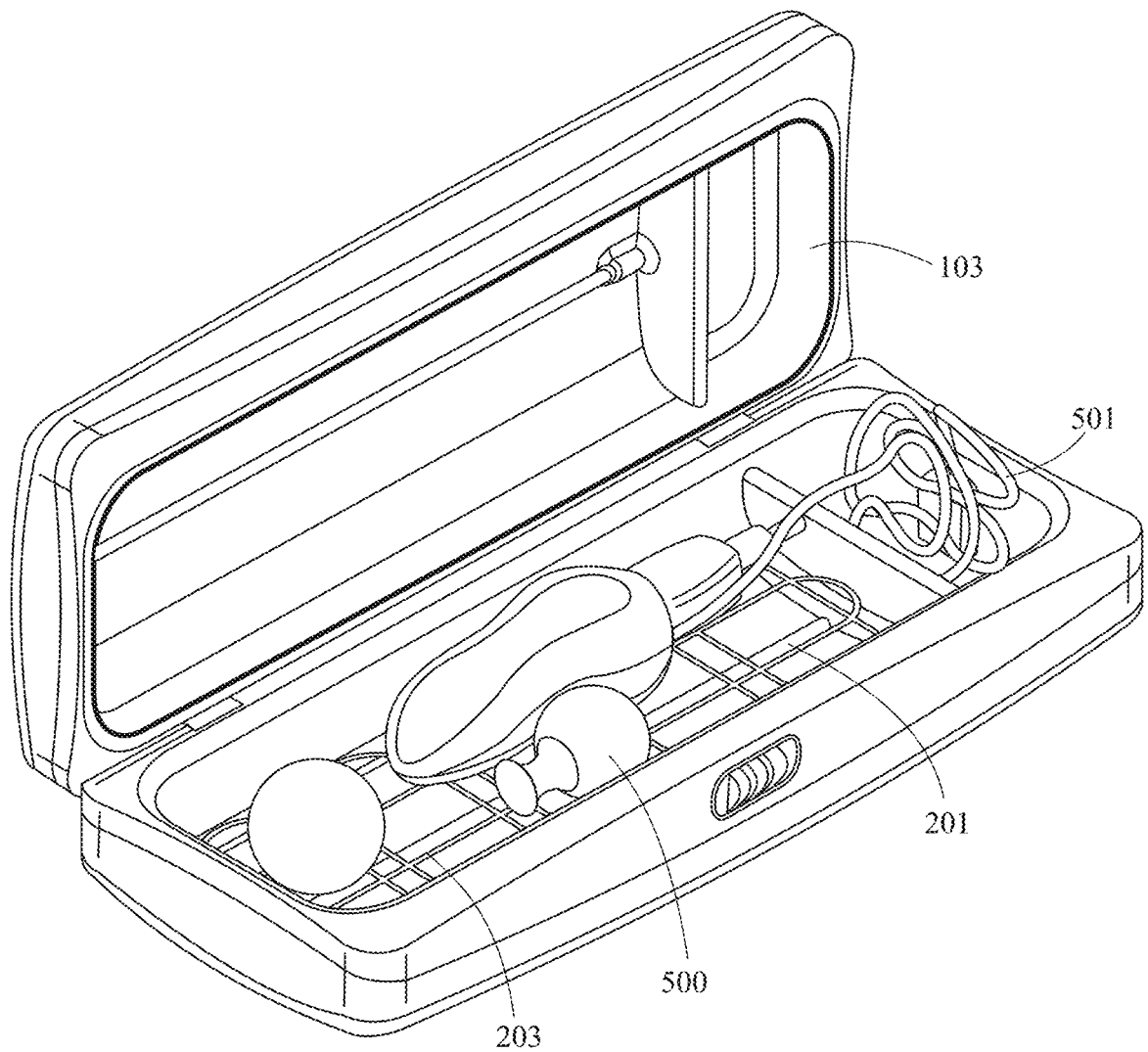
FIG. 12 is a front isometric view of one embodiment of the sanitization apparatus with devices to be sanitized in place.

FIG. 12 is a front isometric view of a similar embodiment of the sanitization apparatus with devices to be sanitized in place. It can be seen that cords 501 of the device 500 are held within recess 103. Moreover, this depiction shows lower emitter 201 disposed below device 500 and grid 203.

Although not depicted in FIG. 12, the apparatus 1 may further comprise a control module, power module, sanitization module, charging module, user interface, and/or other modules as described herein.

Figure 13:
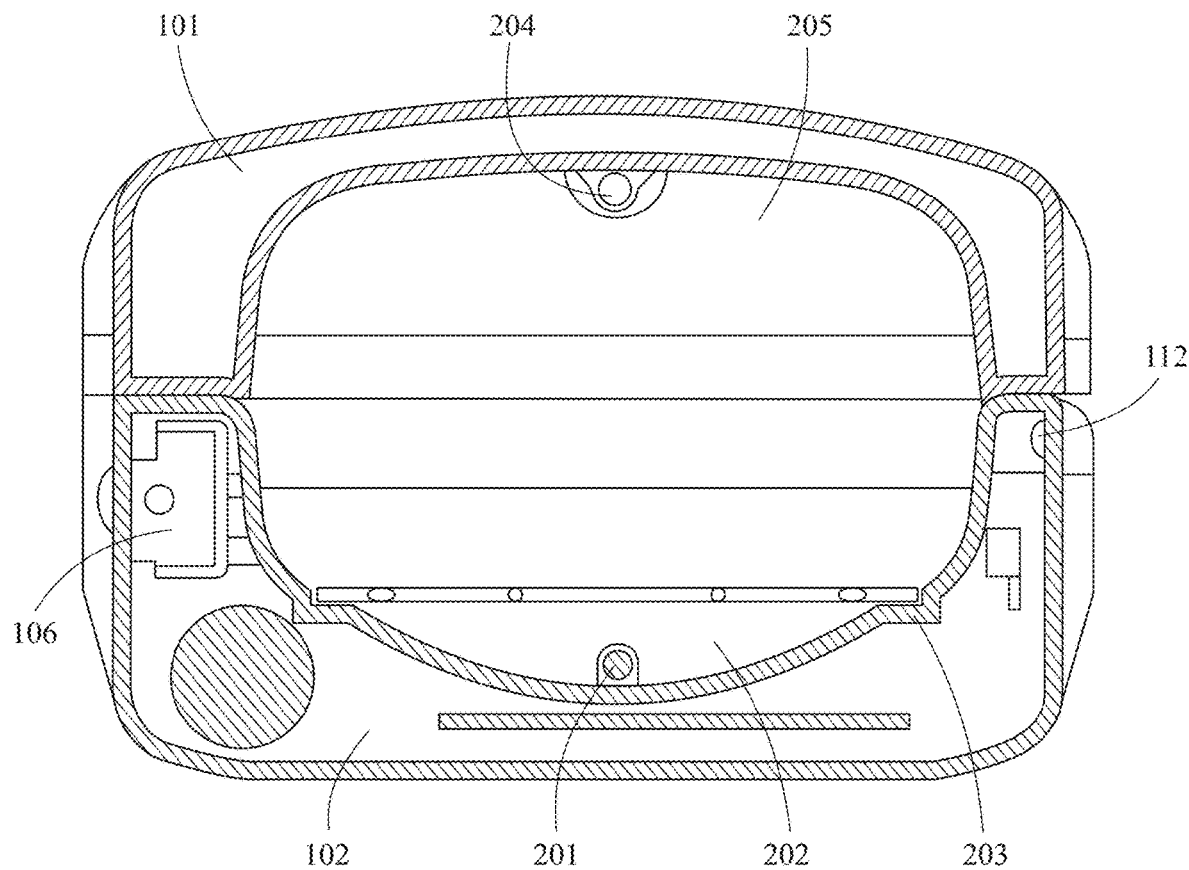
FIG. 13 is a cross-sectional view of one embodiment of the sanitization apparatus.

FIG. 13 is a cross-sectional view of another embodiment of the sanitization apparatus 1. Lower emitter 201 and lower reflector 202 are shown in the lower half 102 of enclosure 100, as is grid 203. Upper emitter 204 and upper reflector 205 are shown in the upper half 101 of enclosure 100, which rotates about hinge 112 to open the apparatus for placement or removal of a device to be sanitized. Lock 106 is in place opposite hinge 112, allowing a user to secure a device within the enclosure if so desired.

Figure 14:
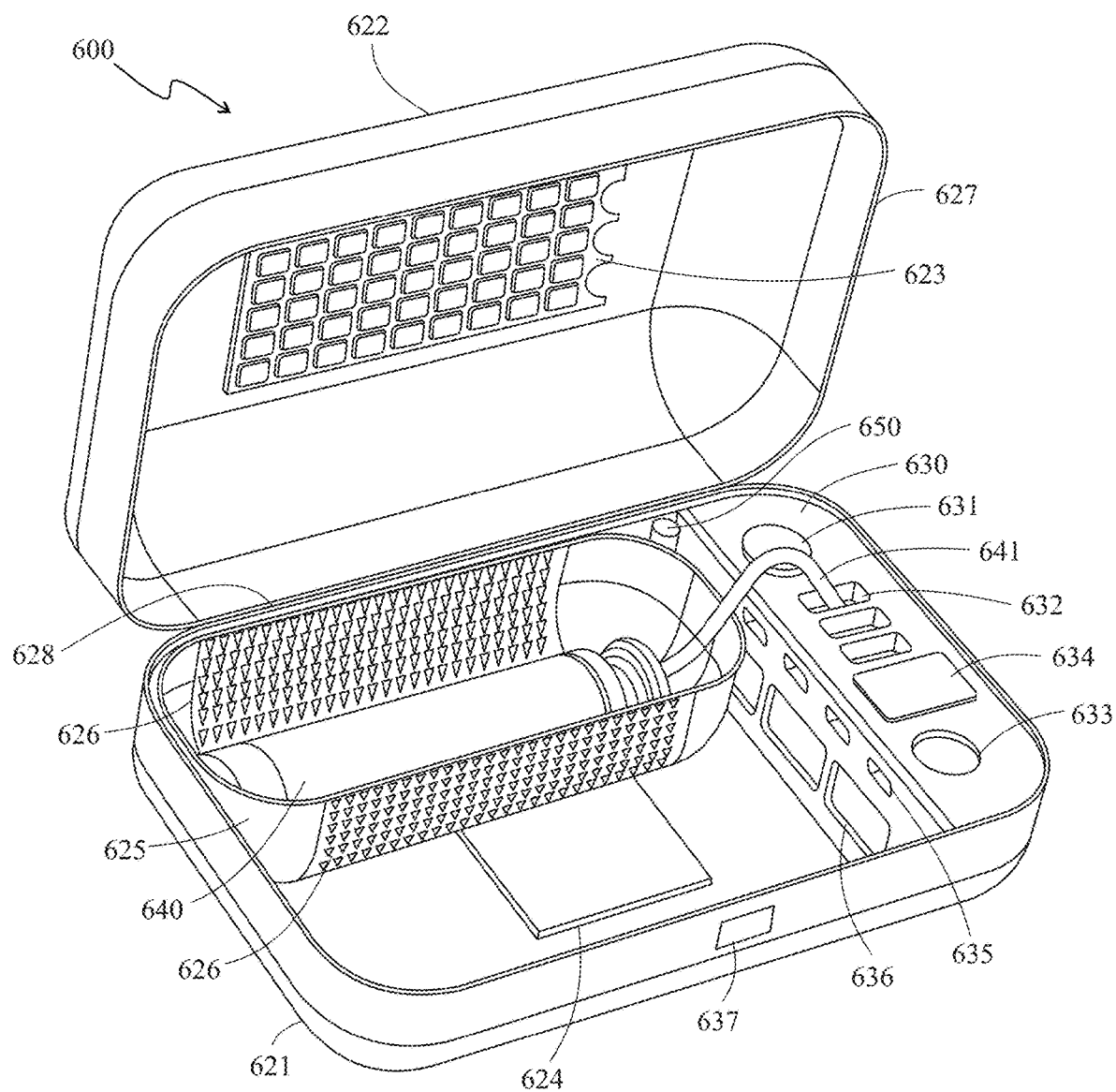
FIG. 14 is a front isometric view of another embodiment of the sanitization apparatus with a device to be sanitized in place.

A front isometric view of another embodiment of the sanitization apparatus 600 with a device 640 to be sanitized in place is shown in FIG. 14. Sanitization apparatus 600 includes an enclosure having an upper member 622 and a lower member 621, at least one emitter (here in the form of a UV LED panel) 623 contained within the upper or lower member 622, 621, and at least one reflective grid (here in the form of a transparent tray 625 having an optional mirrored or reflective prismatic light scattering array) 626 contained within the enclosure for holding or supporting a personal use item. The apparatus 600 may also include an ozone generator ceramic plate 624 contained within the enclosure and a humidifying sponge or humidifying wick 650 contained within the enclosure.

The sanitization apparatus 600 may also include an airtight seal 627 between the upper and lower members 622, 621, a hinge 628 connecting the upper and lower members 622, 621 of the enclosure, a control module 630, at least one knob or button 631 for setting the control module 630, one or more charging ports 632 for charging a personal use item contained within the enclosure, a charging cable 641, an operations indicator 633, an indicator light or digital display 634, one or more small recharging sockets 635, one or more sensors 636, and an exterior ON/OFF switch 637 for activating the apparatus and/or showing status of the apparatus. Knob/button 631 and display 635 may be configured to be on the outside of either the upper or lower member 622, 621.

Figure 15:
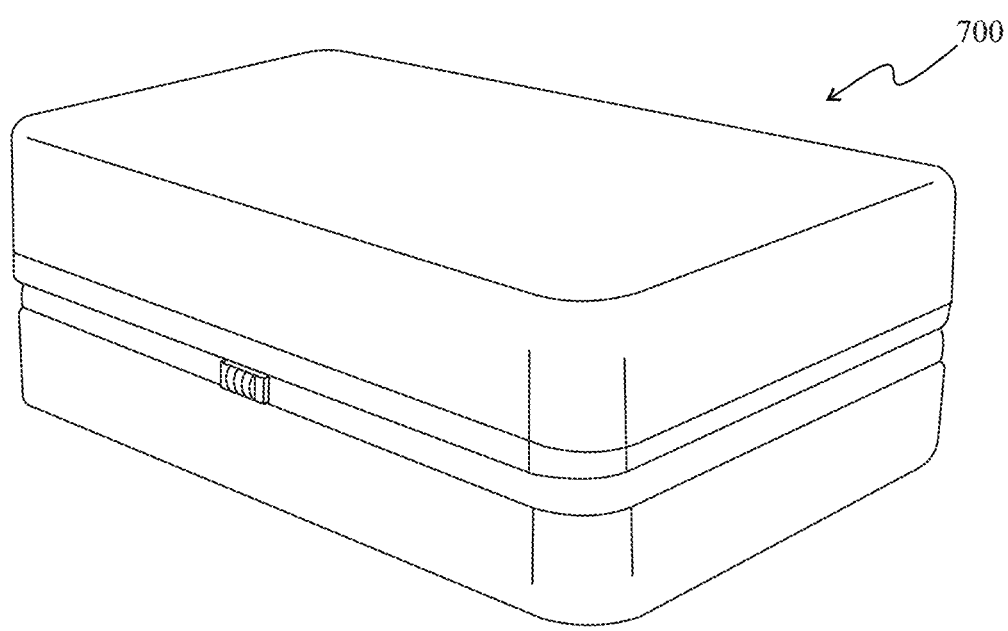
FIG. 15 is a front isometric view of yet another embodiment of the sanitization apparatus shown in a closed configuration.
Figure 16:
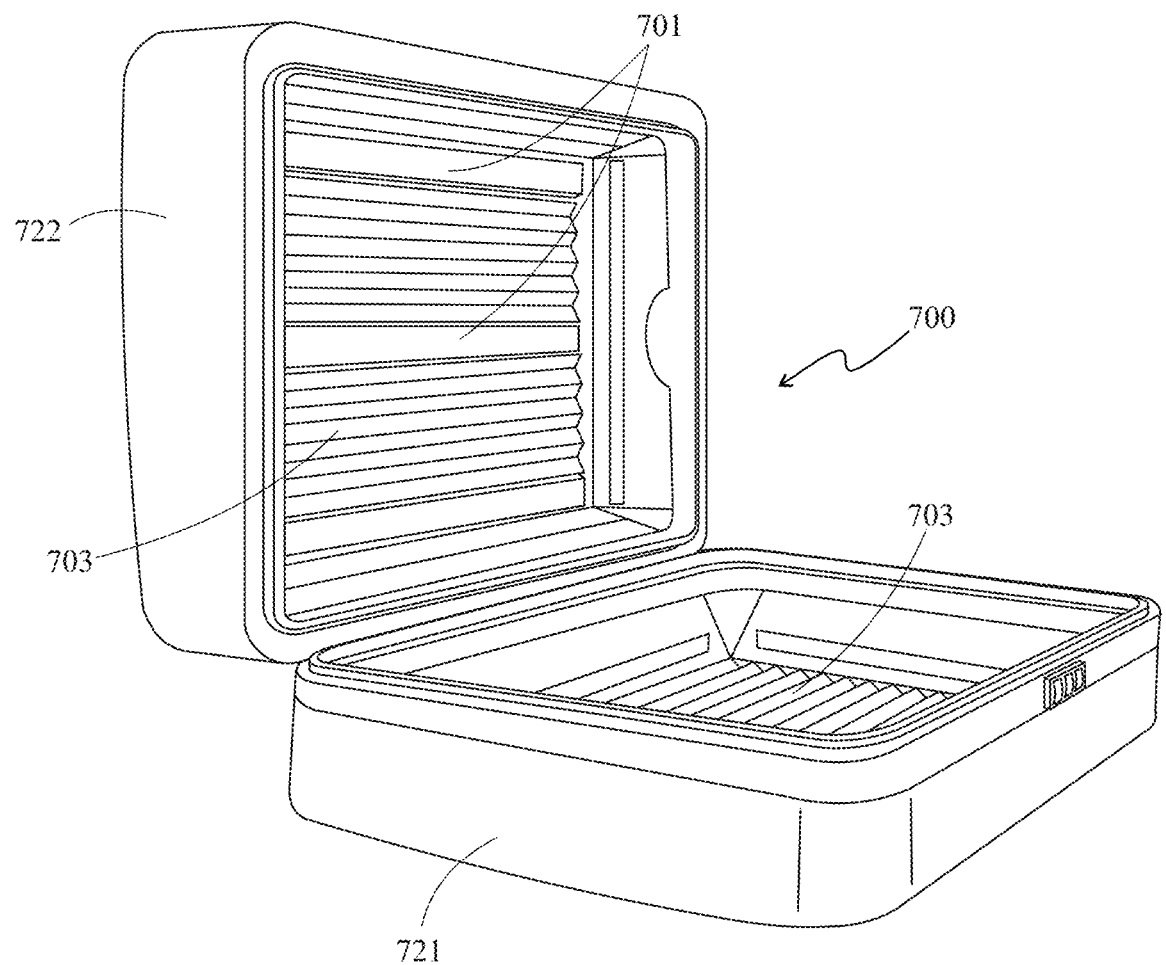
FIG. 16 is a side isometric view of the embodiment of the sanitization apparatus shown in FIG. 15 in an open configuration.

FIG. 15 is a front isometric view of yet another embodiment of the sanitization apparatus 700 shown in a closed configuration and FIG. 16 is a side isometric view of the same embodiment of the sanitization apparatus 700 shown in an open configuration. FIG. 16 shows apparatus 700 with an upper member 722 and a lower member 721, a reflective grid 703 contained within each of the upper and lower members 722, 721, and emitters 701 contained within the upper member 722.

Figure 17:
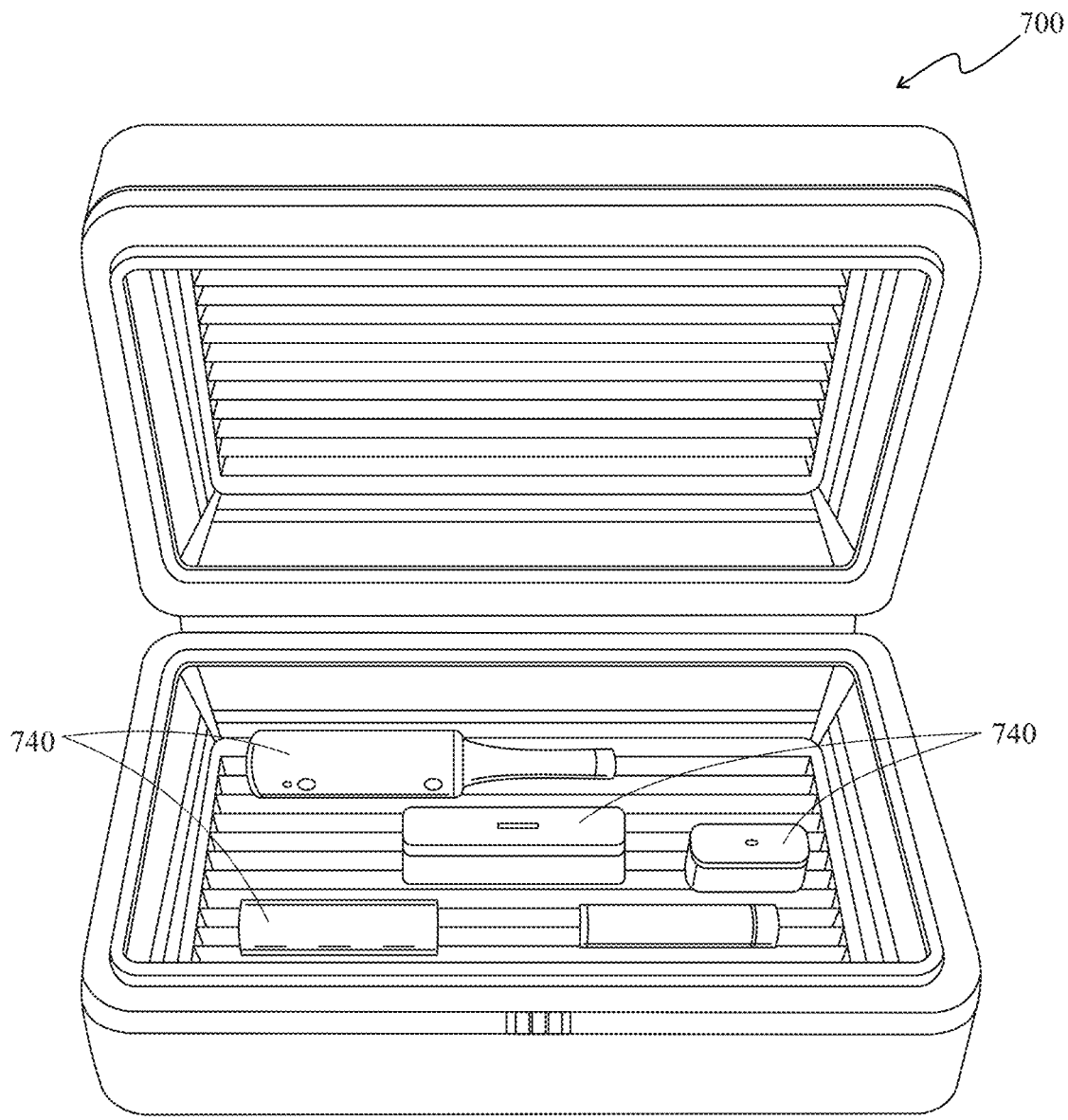
FIG. 17 is a front isometric view of the embodiment of the sanitization apparatus shown in FIGS. 15 and 16 in an open configuration containing personal beauty care items to sanitize.
Figure 18:
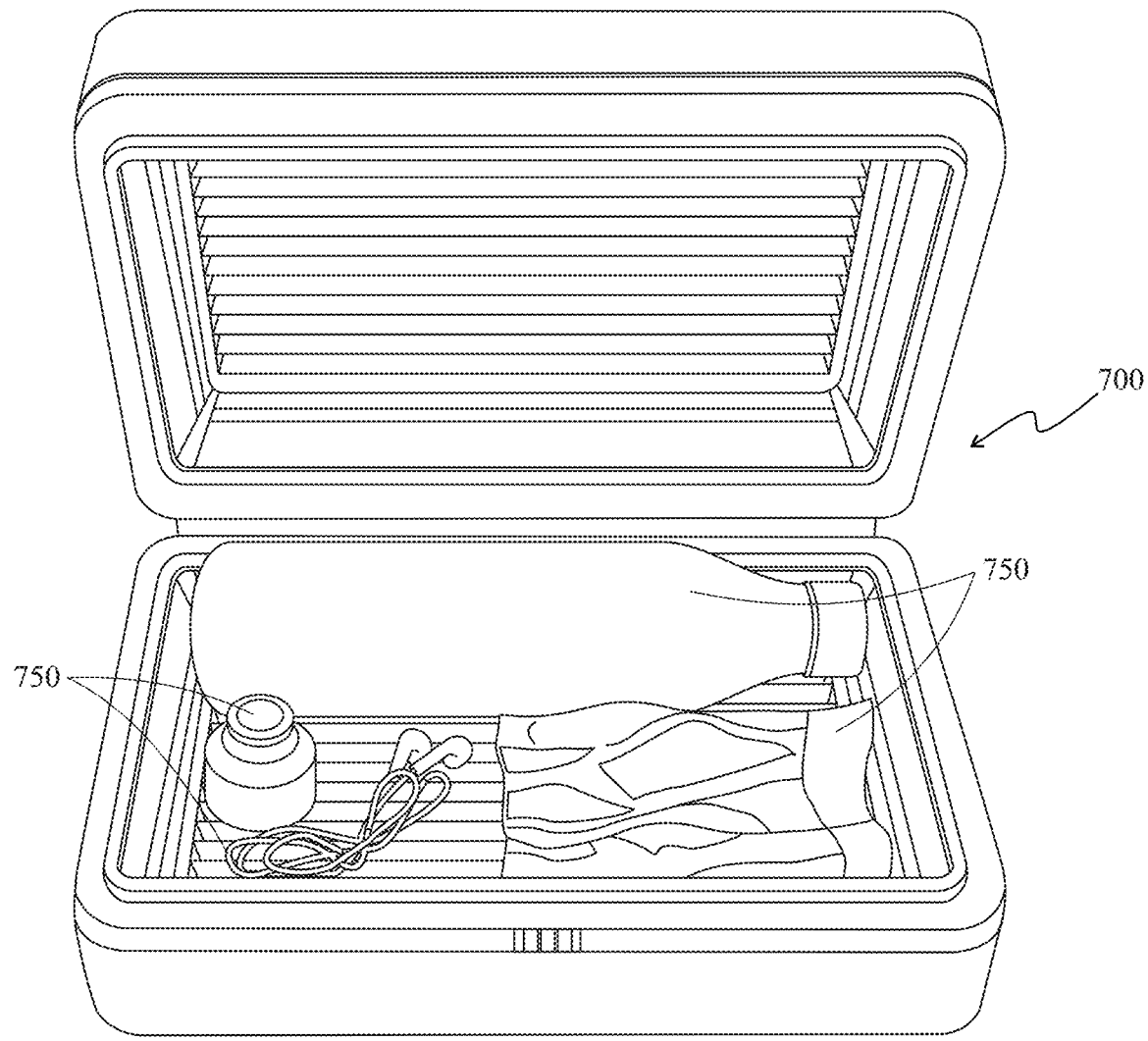
FIG. 18 is a front isometric view of the embodiment of the sanitization apparatus shown in FIGS. 15 and 16 in an open configuration containing water bottle, gloves, ear buds, and other personal use items to sanitize.
Figure 19:
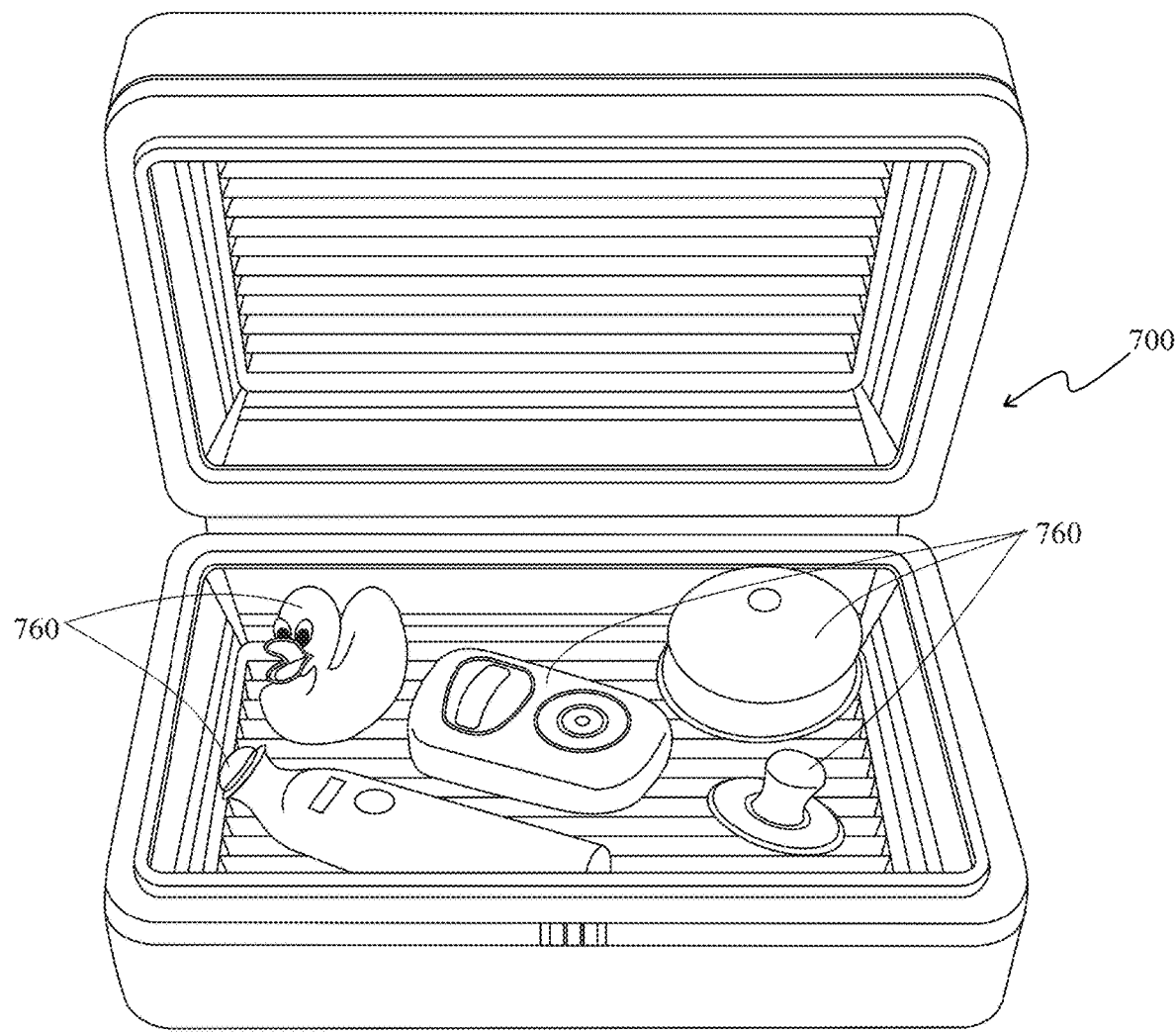
FIG. 19 is a front isometric view of the embodiment of the sanitization apparatus shown in FIGS. 15 and 16 in an open configuration containing a thermometer, children's toy, and other assorted infant care personal use items to sanitize.
Figure 20:
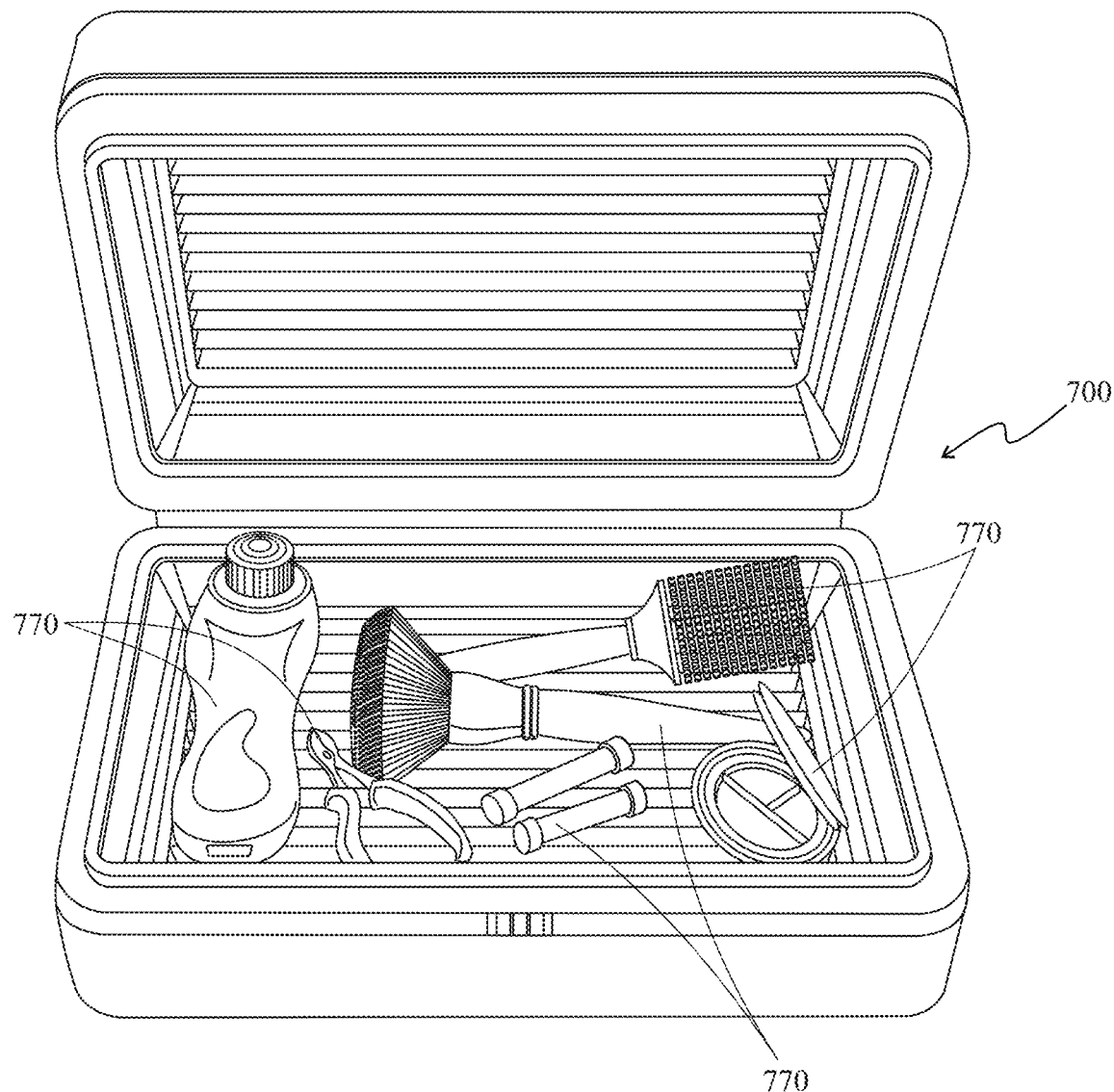
FIG. 20 is a front isometric view of the embodiment of the sanitization apparatus shown in FIGS. 15 and 16 in an open configuration containing nail clipper, makeup, hair brush and other cosmetic personal use items to sanitize.

FIG. 17 is a front isometric view of the embodiment of the sanitization apparatus 700 shown in FIGS. 15 and 16 in an open configuration containing personal beauty care items 740 to sanitize. FIG. 18 is a front isometric view of the embodiment of the sanitization apparatus 700 shown in FIGS. 15 and 16 in an open configuration containing water bottle, gloves, ear buds, and other personal use items 750 to sanitize. FIG. 19 is a front isometric view of the embodiment of the sanitization apparatus 700 shown in FIGS. 15 and 16 in an open configuration containing a thermometer, children's toy, and other assorted infant care personal use items 760 to sanitize. FIG. 20 is a front isometric view of the embodiment of the sanitization apparatus 700 shown in FIGS. 15 and 16 in an open configuration containing nail clipper, makeup, hair brush and other cosmetic personal use items 770 to sanitize.

Figure 21:
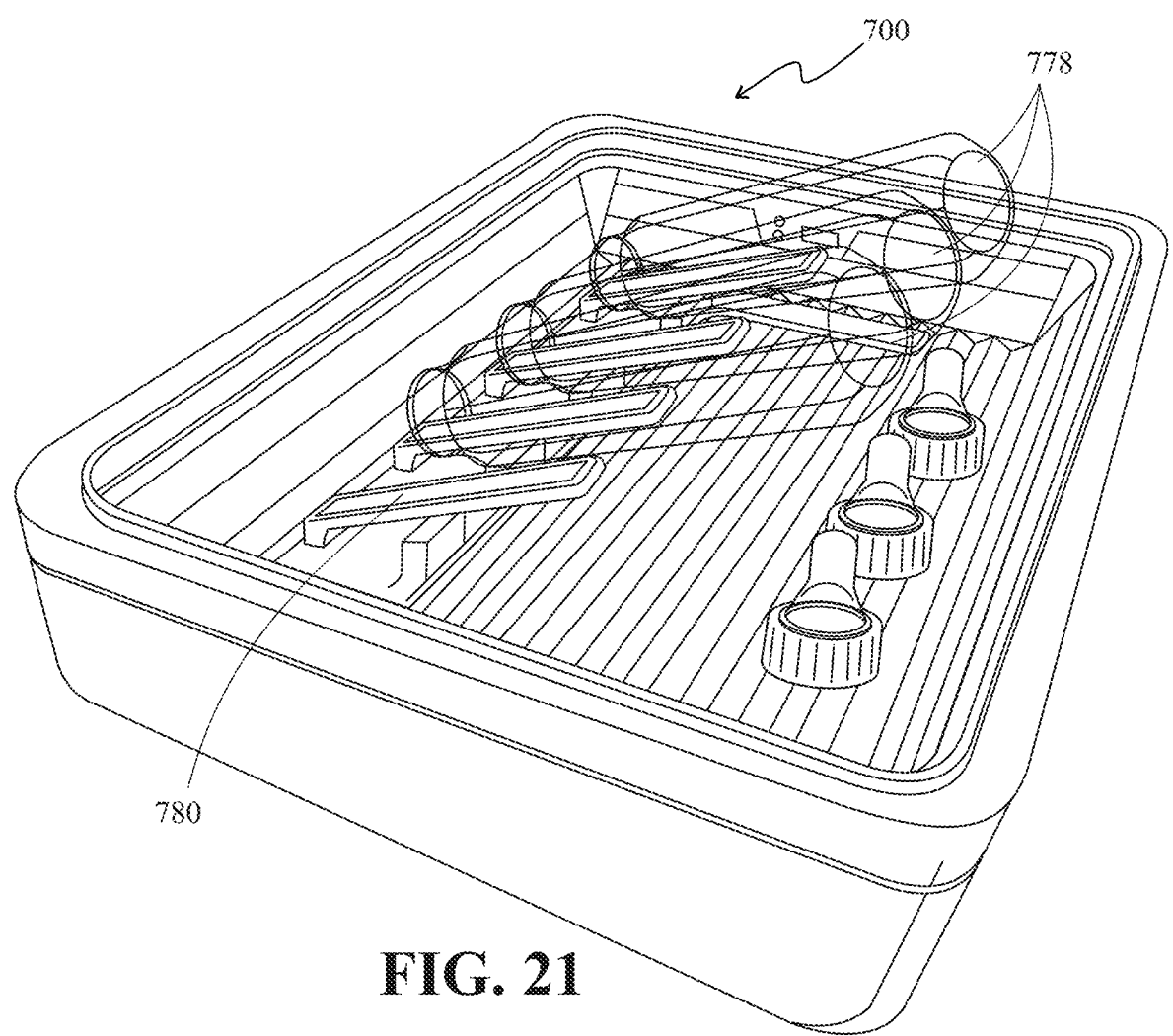
FIG. 21 is a side isometric view of the embodiment of the sanitization apparatus shown in FIGS. 15 and 16 in an open configuration containing a support member in the form of a bottle holder rack and assorted baby bottles to sanitize.
Figure 22:
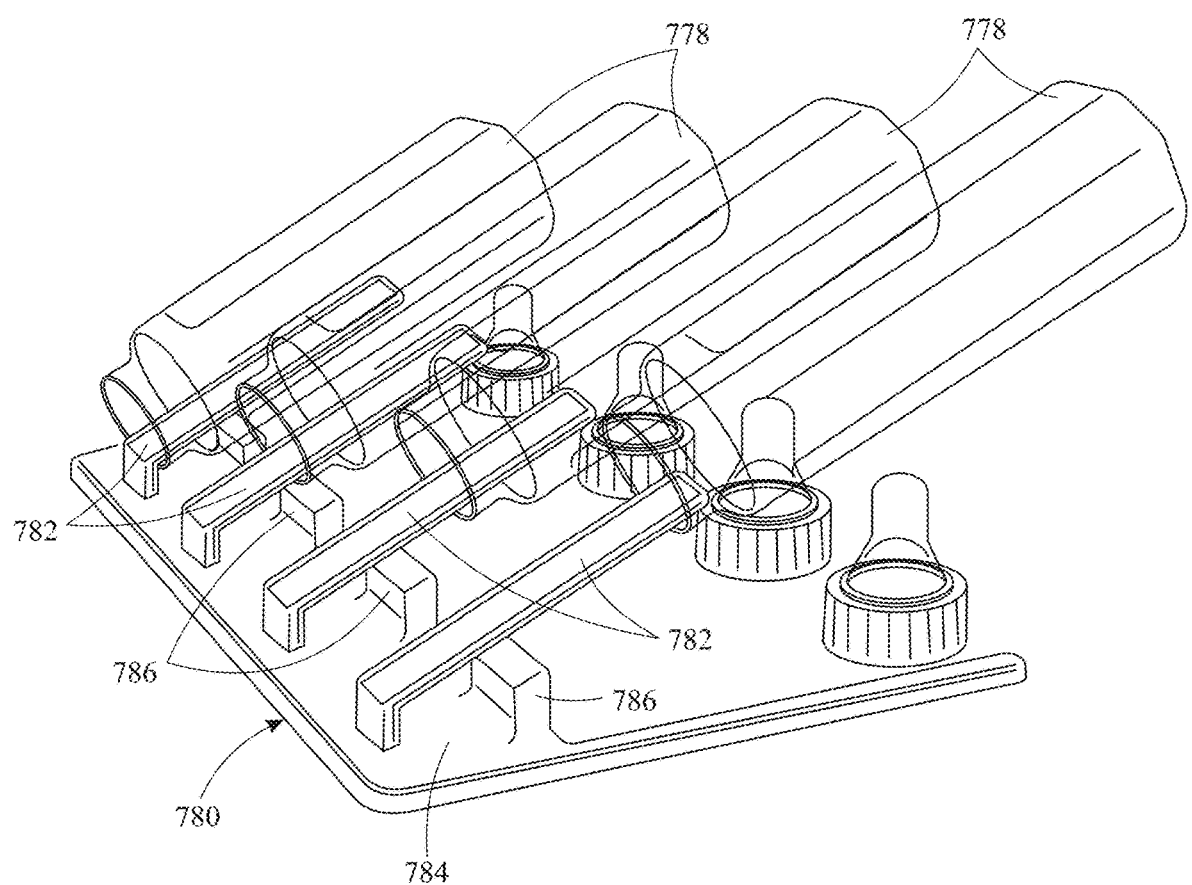
FIG. 22 is an isometric view of the baby bottles and bottle holder rack shown in FIG. 21 shown removed from the apparatus.

FIG. 21 is a side isometric view of the embodiment of the sanitization apparatus 700 shown in FIGS. 15 and 16 in an open configuration containing a support member in the form of a bottle holder rack 780 and assorted baby bottles 778 to sanitize. An isometric view of the baby bottles 778 and bottle holder rack 780 depicted in FIG. 21 are shown removed from the apparatus 700 in FIG. 22. Bottle rack holder 780 functions as an item support member having a plurality of members 782 extending from the item support member 780. The plurality of members 782 may comprise a plurality of raised parallel members that extend along a longest length of the item support member 780. The raised parallel members 782 may be reflective and the item support member 780 may be removable from the apparatus 700. As shown in FIG. 22, the item support member 780 may include a base member 784 with a plurality of transparent rod members 782 extending upward from the base member 784 along a width of the base member (or alternatively a longest length of the base member 784). The base member 784 may further include a plurality of transparent protuberances 786 that extend from the base member 784 such that they are positioned below the plurality of transparent rod members 782.

Figure 23:
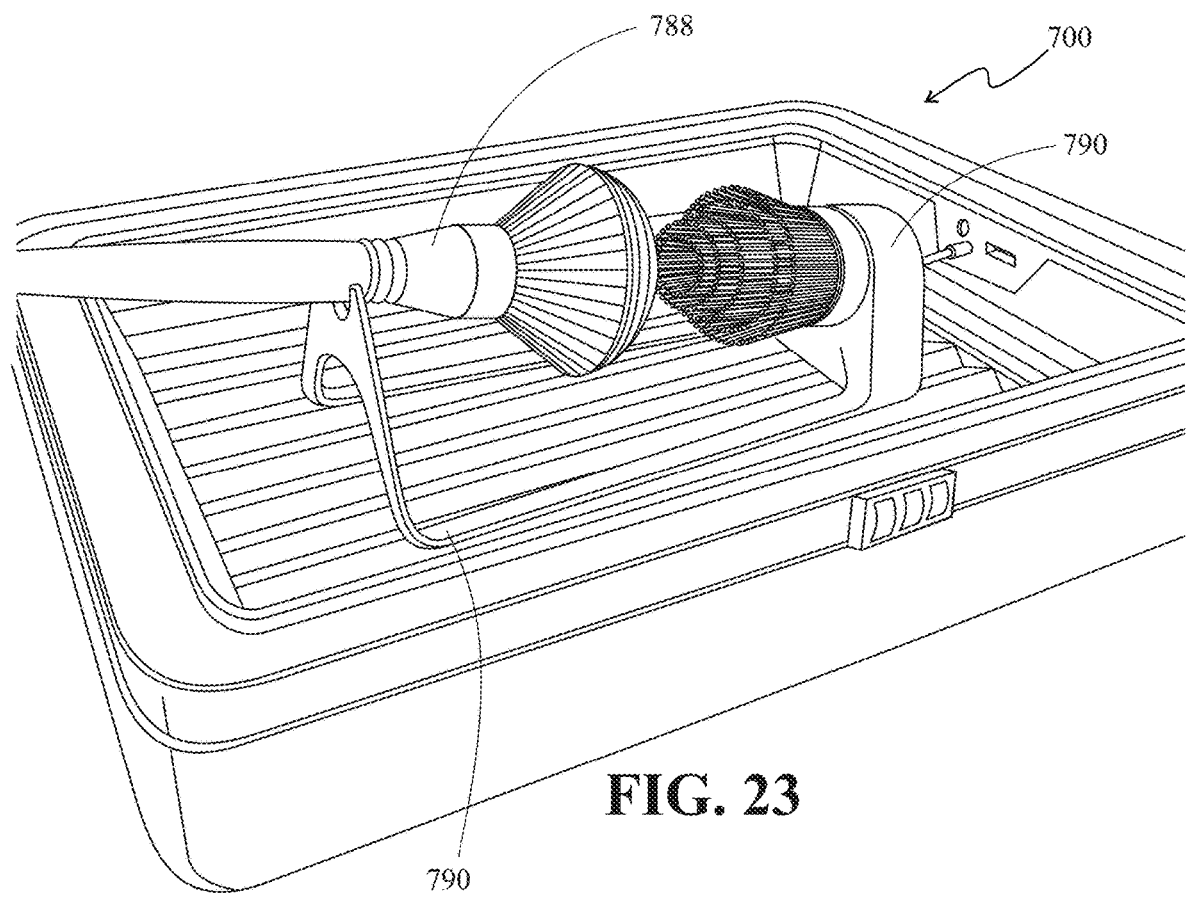
FIG. 23 is a side isometric view of the embodiment of the sanitization apparatus shown in FIGS. 15 and 16 in an open configuration containing a sanitizer brush rack with a brush to sanitize.
Figure 24:
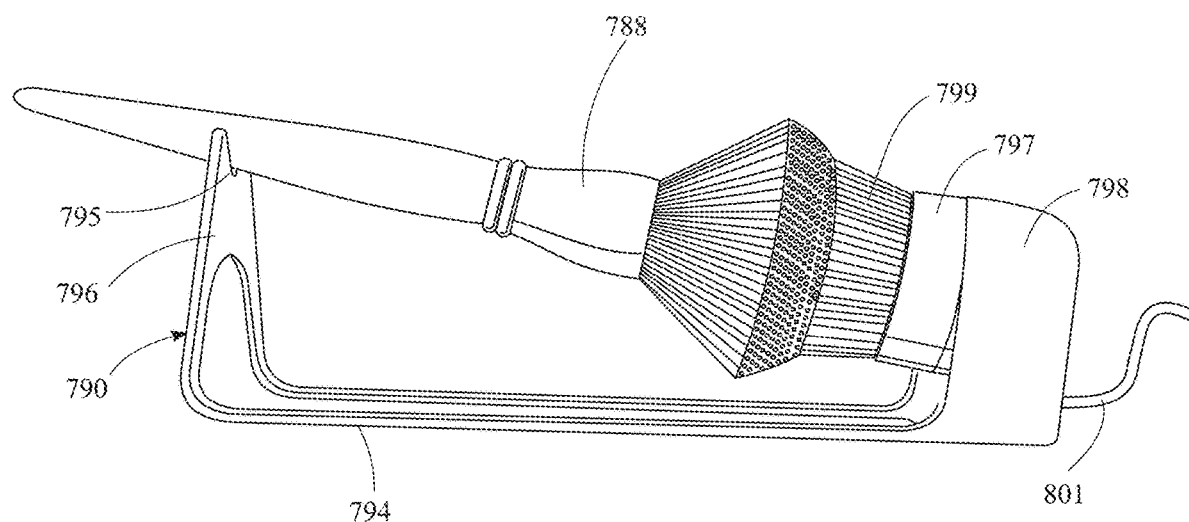
FIG. 24 is a side isometric view of the same sanitizer brush rack with brush shown in FIG. 23 shown removed from the apparatus.
Figure 25:
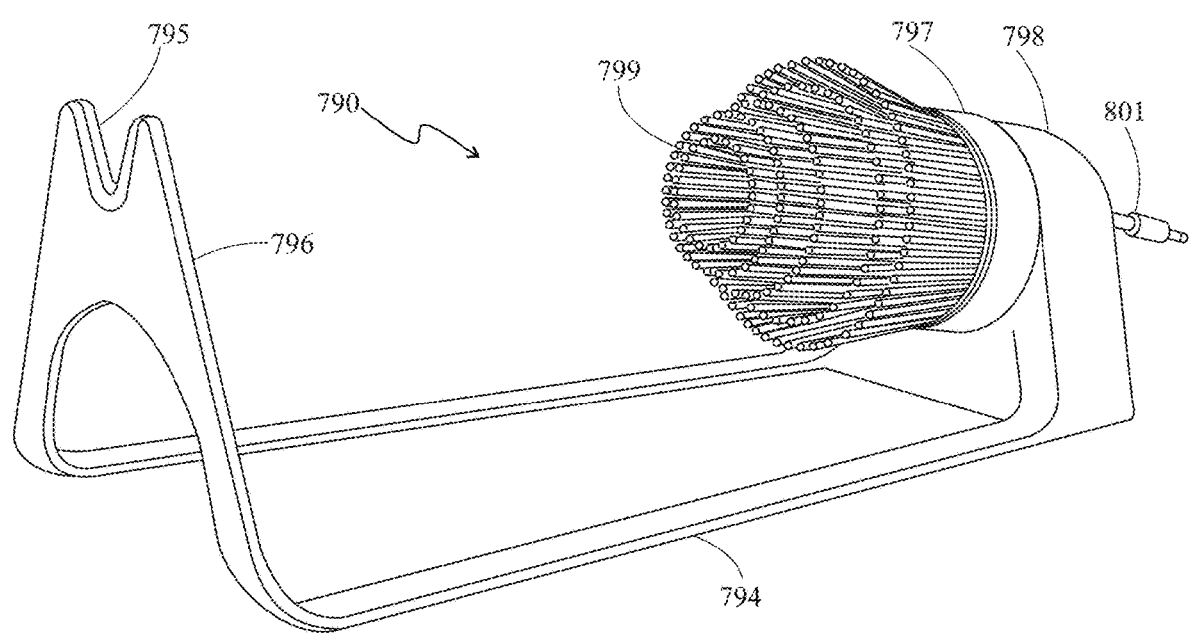
FIG. 25 is an isometric view of the same sanitizer brush rack shown in FIGS. 23 and 24 without the brush to illustrate the UV fiber optics of the sanitizer brush rack.

FIG. 23 is a side isometric view of the embodiment of the sanitization apparatus 700 shown in FIGS. 15 and 16 in an open configuration containing a sanitizer brush rack 790 with a cosmetic brush 788 to sanitize. A side isometric view of the same sanitizer brush rack 790 with cosmetic brush 788 depicted in FIG. 23 is shown removed from the apparatus 700 in FIG. 24. FIG. 25 is an isometric view of the same sanitizer brush rack 790 shown in FIGS. 23 and 24 without the cosmetic brush 788 to illustrate the UV fiber optics of the sanitizer brush rack 790.

Sanitizer brush rack 790 functions as an item support holder and includes a base member 794 having a first end 796 extending upward from the base member 794 and a second end 798 extending upward from the base member 794 and a plurality of transparent fibers 799 extending from the second end 798 of the base member 794. First end 796 of base member 794 may include a notch 795 for retaining the handle of cosmetic brush 788. It will be understood by those skilled in the art that the positioning of the first and second ends of the base member may be reversed such that the plurality of transparent fibers may extend from the first end of the base member and the second end of the base member may include the notch. Further, the end of the base member 794 from which the plurality of transparent fibers 799 extend may include a rotating mechanism 797 which rotates the plurality of transparent fibers 799 during sanitization to ensure that UV light emitted through the transparent fibers 799 reaches all areas of the cosmetic brush 788. The sanitizer brush rack 790 further includes a power cord with plug 801 for connecting the rack 790 to a power source for providing UV or other sanitizing light to the transparent fibers 799 and for providing power to the rotating mechanism 797.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of this subject matter described herein. Furthermore, it is to be understood that the invention is defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.).

While preferred and alternative embodiments of the invention have been illustrated and described, as noted above, many changes can be made without departing from the spirit and scope of the invention. Accordingly, the scope of the invention is not limited by the disclosure of these preferred and alternate embodiments.

The invention claimed is:

1. An apparatus configured to sanitize user devices, the apparatus comprising:
   at least one enclosure comprised of an upper member and a lower member;
   at least one emitter configured to emit electromagnetic radiation, the at least one emitter disposed within, and positioned near an interior surface of, at least one of the upper member or the lower member of the at least one enclosure;
   at least one reflective surface disposed on an interior surface of at least one of the upper member or lower member of the at least one enclosure wherein the at least one reflective surface comprises a plurality of alternating ridges and valleys that reflect the electromagnetic radiation in a plurality of directions; and
   at least one power module configured to power the at least one emitter; and
   at least one control module in communication with the power module and configured to control the apparatus.

2. The apparatus of claim 1 wherein the at least one emitter is in contact with, and disposed between, sections of the at least one reflective surface.

3. The apparatus of claim 2 wherein the at least one reflective surface comprising a plurality of alternating ridges and valleys is disposed on an interior surface of the upper member of the at least one enclosure.

4. The apparatus of claim 3 wherein the at least one reflective surface comprising a plurality of alternating ridges and valleys is also disposed on an interior surface of the lower member of the at least one enclosure.

5. The apparatus of claim 1 wherein the at least one emitter extends along more than half of a length of the interior surface of at least one of the upper member or lower member of the at least one enclosure.

6. A device for sanitizing personal use items comprising:
at least one enclosure;
at least one emitter configured to emit electromagnetic radiation disposed within the at least one enclosure;
an item support contained within the at least one enclosure, the item support having a base member with first and second ends extending upwards from the base member,
at least one power module configured to power the at least one emitter, and
at least one control module to control the device.

7. The device of claim 6 wherein at least one of the first and second ends of the base member includes a notch.

8. The device of claim 6 wherein the item support further comprises a plurality of transparent fibers extending from at least one of the first and second ends of the base member wherein a UV light or other sanitizing light is capable of being emitted through the plurality of transparent fibers.

9. The device of claim 8 wherein the item support further comprises a rotating mechanism which rotates the plurality of transparent fibers.

10. The device of claim 9 further comprising a power cord with connection means for connecting the item support to a power source for providing the UV light or other sanitizing light to the transparent fibers and for providing power to the rotating mechanism.

11. An apparatus configured to sanitize user devices, the apparatus comprising:
at least one enclosure comprised of an upper member and a lower member;
at least one emitter configured to emit electromagnetic radiation, the at least one emitter disposed within at least one of the upper member or the lower member of the at least one enclosure wherein the at least one emitter extends along more than half of a length of an interior of at least one of the upper member and lower member of the at least one enclosure;
at least one reflective grid disposed in at least one of the upper member or the lower member of the at least one enclosure, the at least one reflective grid configured to reflect the electromagnetic radiation in a plurality of directions; and
at least one power module configured to power the at least one emitter; and
at least one control module configured to control the apparatus.

12. The apparatus of claim 11, wherein the at least one enclosure comprised of an upper member and a lower member comprises:
at least one recessed area disposed in at least one of the upper member or the lower member comprising a separate compartment with a separate interior that is separate and apart from an interior area that is in communication with the reflective grid, the at least one recessed area further disposed at one end of the at least one enclosure.

13. The apparatus of claim 12, wherein the at least one recessed area includes at least one charging port for charging the user's device.

14. The apparatus of claim 11, wherein the at least one emitter configured to emit electromagnetic radiation comprises:
at least one emitter configured to emit ultraviolet light.

15. The apparatus of claim 11, wherein the at least one emitter configured to emit electromagnetic radiation comprises:
a first emitter disposed in the upper member of the at least one enclosure; and
a second emitter disposed in the lower member of the at least one enclosure.

16. The apparatus of claim 11, further comprising at least one reflective surface disposed within at least one of the upper member or the lower member of the at least one enclosure.

17. The apparatus of claim 16, wherein the at least one reflective surface disposed within at least one of the upper member or the lower member of the at least one enclosure comprises at least one reflective surface with a plurality of alternating ridges and valleys.

18. The apparatus of claim 11, wherein the at least one power module configured to power the at least one emitter comprises:
at least one power source;
at least one transmission mechanism disposed between the at least one power source and the at least one emitter; and
at least one switch mechanism configured to control the flow of electricity along the at least one transmission mechanism.

19. The apparatus of claim 11, wherein the at least one power module configured to power the at least one emitter comprises at least one charging module configured to be removably coupleable with at least one user device.

20. The apparatus of claim 11, wherein the at least one control module configured to control the apparatus comprises at least one user interface configured to receive user input.

* * * * *